US008741310B2

(12) United States Patent
Chen et al.

(10) Patent No.: US 8,741,310 B2
(45) Date of Patent: Jun. 3, 2014

(54) FUSION-INTERMEDIATE STATE OF HIV-1 GP41 TARGETED BY BROADLY NEUTRALIZING ANTIBODIES

(75) Inventors: Bing Chen, Chestnut Hill, MA (US);
Gary H. Frey, Nashua, NH (US);
Stephen C. Harrison, Brighton, MA (US)

(73) Assignees: Children's Medical Center Corporation, Boston, MA (US);
President and Fellows of Harvard College, Cambridge, MA (US); Howard Hughes Medical Institute, Chevy Chase, MD (US)

( * ) Notice: Subject to any disclaimer, the term of this patent is extended or adjusted under 35 U.S.C. 154(b) by 508 days.

(21) Appl. No.: 12/869,967

(22) Filed: Aug. 27, 2010

(65) Prior Publication Data

US 2011/0086041 A1    Apr. 14, 2011

Related U.S. Application Data

(63) Continuation of application No. PCT/US2009/035459, filed on Feb. 27, 2009.

(60) Provisional application No. 61/032,520, filed on Feb. 29, 2008, provisional application No. 61/032,732, filed on Feb. 29, 2008.

(51) Int. Cl.
*A61K 39/21*    (2006.01)

(52) U.S. Cl.
USPC ..................................... 424/208.1

(58) Field of Classification Search
None
See application file for complete search history.

(56) References Cited

U.S. PATENT DOCUMENTS

| | | | |
|---|---|---|---|
| 5,087,557 | A | 2/1992 | McClure |
| 6,602,705 | B1 | 8/2003 | Barnett et al. |
| 2003/0138440 | A1 | 7/2003 | Fang et al. |
| 2004/0137429 | A1 | 7/2004 | Epstein et al. |
| 2004/0213801 | A1 | 10/2004 | Wild et al. |

OTHER PUBLICATIONS

Gallo, R. C, Nov. 2005, The end or the beginning of the drive to an HIV-preventive vaccine: a view from over 20 years, The Lancet 366(9500):1894_1898.*
Walker, B. D., and D. R. Burton, May 2008, Toward an AIDS vaccine, Science 320:760-764.*
Burton, D. R., et al., Mar. 2004, HIV vaccine design and the neutralizing antibody problem, Nat. Immunol. 5(3):233-236.*
Levine, A. J., Dec. 2008, Why do we not yet have a human immunodeficiency virus vaccine, J. Virol. 82(24):11998-12000.*
International Search Report/Written Opinion relating to corresponding PCT/US2009/035459.
Nelson, et al., "An Affinity-Enhanced Neutralizing Antibody Against the Membrane-Proximal External Region of Human Immunodeficiency Virus Type 1 and gp41 Recognizes and Epitope Between Those of 2F5 and 4E10," Journal of Virology, Apr. 2007, vol. 81, No. 8, 4033-4043.
Roche, et al.,"Structure of the Prefusion Form of the Vesicular Stomatitis Virus Glycoprotein G," Science, Feb. 9, 2007, vol. 315, 846-848.
Steger, et al., "Kinetic Dependence to HIV-1 Entry Inhibition," Journal of Biological Chemistry, Sep. 1, 2006, vol. 281, No. 35, 25813-25821.
Follis, et al., "Genetic Evidence that Interhelical Packing Interactions in the gp41 Core Are Critical for Transition of the Human Immunodeficiency Virus Type 1 Envelope Glycoprotein to the Fusion-Active State," Journal of Virology, Jul. 2002, vol. 76, No. 14, p. 7356-7362.
Cardoso, et al.,"Broadly Neutralizing Anti-HIV Antibody 4E10 Recognizes a Helical Conformation of a Highly Conserved Fusion-Associated Motif in gp41," Immunity, Feb. 2005, vol. 22, 163-173.
Munoz-Barroso, et al.,"Dilation of the Human Immunodeficiency Virus-1 Envelope Glycoprotein Fusion Pore Revealed by the Inhibitory Action of a Synthetic Peptide from gp41," The Journal of Cell Biology, Jan. 26, 1998, vol. 140, No. 2, 315-323.
Wei, et al.,"Antibody neutralization and escape by HIV-1," Nature, Mar. 20, 2003, vol. 422, 307-312.
Trkola, et al., "Human Monoclonal Antibody 2G12 Defines a Distinctive Neutralization Epitope on the gp120 Glycprotein of Human Immunodeficiency Virus Type 1," Journal of Virology, Feb. 1996, vol. 70, No. 2, p. 1100-1108.
Muster, et al.,"A Conserved Neutralizing Epitope on gp41 of Human Immunodeficiency Virus Type 1," Journal of Virology, Nov. 1993, vol. 67, No. 11, p. 6642-6647.
Binley, et al., "Comprehensive Cross-Clade Neutralization Analysis of a Panel of Anti-Human Immunodeficiency Virus Type 1 Monoclonal Antibodies," Journal of Virology, Dec. 2004, vol. 78, No. 23, p. 13232-13252.
Rits-Volloch, et al., "Restraining the conformation of HIV-1 gp120 by removing a flexible loop," The EMBO Journal (2006) 25, 5026-5035.

(Continued)

*Primary Examiner* — Jeffrey Parkin
(74) *Attorney, Agent, or Firm* — Edwards Wildman Palmer LLP; Peter F. Corless

(57) ABSTRACT

Isolated, antigenic polypeptides including a prehairpin intermediate conformation of gp41 and vectors encoding such polypeptides are provided. Antibodies that bind to a prehairpin intermediate conformation of gp41 and methods of making antibodies a that bind to prehairpin intermediate conformation of gp41 are also provided. Vaccines against a prehairpin intermediate conformation of gp41, as well as methods of treating subjects infected with HIV, preventing HIV infection, and inhibiting HIV-mediated activities are also provided. Methods of screening compounds that bind to an isolated, prehairpin intermediate conformation of gp41 are further provided.

6 Claims, 20 Drawing Sheets
(20 of 20 Drawing Sheet(s) Filed in Color)

(56) References Cited

OTHER PUBLICATIONS

Miller, et al, "A human monoclonal antibody neutralizes diverse HIV-1 isolates by binding a critical gp41 epitope," PNAS, Oct. 11, 2005, vol. 102, No. 41, 14759-14764.
Chan, et al., "HIV Entry and Its Inhibition," Cell, May 29, 1998, vol. 93, 681-684.
Kilby, et al., "Novel Therapies Based on Mechanisms of HIV-1 Cell Entry," The New England Journal of Medicine, May 29, 2003, vol. 348, 2228-2238.
Eckert, et al., "Inhibiting HIV-1 Entry: Discovery of D-Peptide Inhibitors that Target the gp41 Coiled-Coil Pocket," Cell, vol. 99, Oct. 1, 1999, 103-115.
Root, et al., "Protein Design of an HIV-1 Entry Inhibitor," Science, Feb. 2, 2001, vol. 291, 884-888.
Schulke, et al., "Oligomeric and Conformational Properties of a Proteolytically Mature, Disulfide-Stabilized Human Immunodeficiency Virus Type 1 gp140 Envelope Glycoprotein," Journal of Virology, Aug. 2002, vol. 76, No. 15, p. 7760-7776.
Hart, et al., "Glycosylation inhibitors and neuraminidase enhance human immunodeficiency virus type 1 binding and neutralization by mannose-binding lectin," Journal of General Virology (2003), 84, 353-360.
Dey, et al., "Specific amino acids in the N-terminus of the gp41 ectodomain contribute to the stabilization of a soluble, cleaved gp140 envelope glycoprotein from human immunodeficiency virus type 1," Virology, Mar. 30, 2007, 360(1), 199-208.
Rosny, et al., "Binding of the 2F5 Monoclonal Antibody to Native and Fusion-Intermediate Forms of Human Immunodeficiency Virus Type 1 gp41: Implications for Fusion-Inducing Conformational Charges," Journal of Virology, Mar. 2004, vol. 78, No. 5, p. 2627-2631.
Frey, et al., "Small molecules that bind the inner core of gp41 and inhibit HIV envelope-mediated fusion," PNAS, Sep. 19, 2006, vol. 103, No. 38, 13938-13943.
Nelson, et al., "An Affinity-Enhanced Neutralizing Antibody against the Membrane-Proximal External Region of Human Immunodeficiency Virus Type 1 gp41 Recognizes an Epitope between Those of 2F5 and 4E10," Journal of Virology, Apr. 2007, vol. 81, No. 8, p. 4033-4043.
Burton, et al., "Efficient Neutralization of Primary Isolates of HIV-1 by a Recombinant Human Monoclonal Antibody," Science, Nov. 11, 1994, vol. 266, 1024-1027.
Haynes, et al., "Cardiolipin Polyspecific Autoreactivity in Two Broadly Neutralizing HIV-1 Antibodies," Science, Jun. 24, 2005, vol. 308, 1906-1908.
Gorny, et al., "Recognition by Human Monoclonal Antibodies of Free and Complexed Peptides Representing the Prefusogenic and Fusogenic Forms of Human Immunodeficiency Virus Type 1 gp41," Journal of Virology, Jul. 2000, vol. 74, No. 13, p. 6186-6192.
Ofek, et al., "Structure and Mechanistic Analysis of the Anti-Human Immunodeficieny Virus Type 1 Antibody 2F5 in Complex with Its gp41 Epitope," Journal of Virology, Oct. 2004, vol. 78, No. 19, p. 10724-10737.
Cavacini, et al., "Interactions of human antibodies, epitope exposure, antibody binding and neutralization of primary isolate HIV-1 virions," AIDS 2002, 16: 2409-2417.
Chambers, et al., "Heptad repeat sequences are located adjacent to hydrophobic regions in several types of virus fusion glycoproteins," Journal of General Virology (1990), 71, 3075-3080.
Yang, et al., "Highly Stable Trimmers Formed by Human Immunodeficiency Virus Type 1 Envelope Glycoproteins Fused with Trimeric Motif of T4 Bacteriophage Fibritin," Journal of Virology, May 2002, vol. 76, No. 9, p. 4634-4642.
Chen, et al., "A Chimeric Protein of Simian Immunodeficiency Virus Envelope Glycoprotein gp140 and *Esherichia coli* Aspartate Transcarbamoylase," Journal of Virology, May 2004, vol. 78, No. 9, p. 4508-4516.
Daniels, et al., "Analyses of the Antigenicity of Influenza Haemagglutinin at the pH Optimum for Virus-mediated Membrane Fusion," Journal of General Virology (1983) 64, 1657-1662.
Modis, et al., "Structure of the dengue virus envelope protein after membrane fusion," Nature, Jan. 22, 2004, vol. 427, 313-319.
Chen, et al., "Expression, Purification, and Characterization of gp160e, the Soluble, Trimeric Ectodomain of the Simian Immunodeficiency Virus Envelope Glycoprotein, gp160," Journal of Biological Chemistry, Nov. 10, 2000, vol. 275, No. 45, 34946-34953.
Binley, et al., "Enhancing the Proteolytic Maturation of Human Immunodeficiency Virus Type 1 Envelope Glycoproteins," Journal of Virology, Mar. 2002, vol. 76, No. 6, p. 2606-2616.
Binley, et al., "Redox-Triggered Infection by Disulfide-Shackled Human Immunodeficiency Virus Type 1 Pseudovirions," Journal of Virology, May 2003, vol. 77, No. 10, p. 5678-5684.
Zhou, et al., "Structural definition of a conserved neutralization epitope on HIV-1 gp120," Nature, Feb. 15, 2007, 445(7129): 732-737.
Thali, et al., "Characterization of Conserved Human Immunodeficiency Virus Type 1 gp120 Neutralization Epitopes Exposed upon gp120-CD4 Binding," Journal of Virology, Jul. 1993, vol. 67, No. 7, p. 3978-3988.
Xu, et al., "Epitope Mapping of Two Immunodominant Domains of gp41, the Transmembrane Protein of Human Immunodeficiency Virus Type 1, Using ten Human Monoclonal Antibodies," Journal of Virology, Sep. 1991, vol. 65, No. 9, p. 4832-4838.
Kim, et al., "The Stoichiometry of Trimeric SIV Glycoprotein Interaction with CD4 Differs from That of Anti-envelope Antibody Fab Fragments," The Journal of Biological Chemistry, vol. 276, No. 46, 16, Nov. 2001, pp. 42667-42676.
Nyambi, et al., "Conserved and Exposed Epitopes on Intact, Native, Primary Human Immunodeficiency Virus Type 1 Virions of Group M," Journal of Virology, Aug. 2000, vol. 74, No. 15, p. 7096-7107.
Finnegan, et al., "Antigenic Properties of the Human Immunodeficiency Virus Transmembrane Glycoprotein during Cell-Cell Fusion," Journal of Virology, Dec. 2002, vol. 76, No. 23, p. 12123-12134.
Sattentau, et al., "Epitope Exposure on Functional Oligomeric HIV-1 gp41 Molecules," Virology 206, 713-717 (1995).
Ohi, et al., "Negative Staining and Image Classification—Powerful Tools in Modem Electron Microscopy," Biol.Proced. Online 2004; 6(1):23-34.
Lupas, "Coiled Coils: New structures and new functions," TIBS 21—Oct. 1996, 375-382.
Ho, et al., "Conformational constraints imposed on a pan-neutralizing HIV-1 antibody epitope result in increased antigenicity but not neutralizing response," Vaccine 23 (2005) 1559-1573.
Harrison, "Mechanism of Membrane Fusion by Viral Envelope Proteins," Advances in Virus Research vol. 64 (2005).
Frank, et al., "SPIDER and WEB: Processing and Visualization of Images in 3D Electron Microscopy & Related Fields," Journal of Structural Biology 116, No. 30, 190-199 (1996).
Dimitrov, et al., "Exposure of the Membrane-Proximal External Region of HIV-1 gp41 in the course of HIV-1 Envelope Glycoprotein-Mediated Fusion," Biochemistry 2007, 46, 1398-1401.
Bower, et al., "HIV-1 Env gp140 Trimerselicit Neutralizing Antibodies Without Efficient Induction of Conformational Antibodies," Vaccine 24 (2006) 5442-5451.
Skehel, et al., Receptor Binding and Membrane Fusion in Virus Entry: The Influenza Hemagglutinin, Annu. Rev. Biochem 2000, 69:531-69.

* cited by examiner

```
92UGgp140-Fd       ------EESQKQQEKNEQELLELDKWANLWNWFDISNWLWYIK---Fd
HXB2gp41interf     ------EESQNQQEKNEQELLELDKWASLWNWFNITNWLWYIK---GCN4
92UGgp41inter      ------EESQKQQEKNEQELLELDKWANLWNWFDISNWLWYIK---Fd
92UGgp41post       ------EESQKQQEKNEQELLELDKWANL
2F5 epitope peptide            ELLELDKWASL
4E10 epitope peptide                     SLWNWFNITNWLWYIK
```

FUSION-INTERMEDIATE STATE OF HIV-1 GP41 TARGETED BY BROADLY NEUTRALIZING ANTIBODIES

RELATED APPLICATIONS

This application is a continuation of PCT/US2009/035459, filed Feb. 27, 2009 which claims priority from U.S. provisional patent application No. 61/032,732, filed Feb. 29, 2008, and U.S. provisional patent application No. 61/032,520, filed Feb. 29, 2008, each of which is hereby incorporated herein by reference in its entirety for all purposes.

STATEMENT OF GOVERNMENT INTERESTS

This invention was made with government support under National Institutes of Health grant numbers R21 AI069972 and U01 AI067854. The Government has certain rights in the invention.

FIELD

The present invention relates to methods and compositions for neutralizing viral infection, for example, infection by HIV (e.g., HIV-1).

BACKGROUND

HIV-1 infection generally induces a strong antibody response to the envelope glycoprotein (i.e., trimeric $(gp160)_3$, cleaved to $(gp120/gp41)_3$), the sole antigen on the virion surface. Most of the induced antibodies are ineffective in preventing infection, however, as they are either non-neutralizing or narrowly isolate-specific, and the virus replicates so rapidly that ongoing selection of neutralization-resistant mutants allows viral evolution to "keep ahead" of high-affinity antibody production (Wei et al. (2003) *Nature* 422:307). Moreover, much of the antibody response may be to rearranged or dissociated forms of gp120 and gp41, on which the dominant epitopes may be either in hypervariable loops or in positions occluded on virion-borne envelope trimer. A few rare "broadly neutralizing" antibodies have been detected that recognize one of three relatively conserved regions on the envelope protein: the CD4 binding site (mAb b12) (Burton et al. (1994) *Science* 266: 1024); carbohydrates on the outer gp120 surface (mAb 2G12) (Trkola et al. (1996) *J. Virol.* 70:1100); and a segment of the gp41 ectodomain adjacent to the viral membrane (mAbs 2F5 and 4E10) (Muster et al. (1993) *J. Virol.* 67:6642; Stiegler et al. (2001) *AIDS Res. Hum. Retroviruses* 17:1757), often called the membrane-proximal external region ("MPER"). Understanding the molecular mechanisms of neutralization by these and other antibodies could help design immunogens to induce them.

Fusion of viral and target cell membranes initiates HIV-1 infection. Conformational changes in gp120 that accompany its binding to receptor (CD4) and co-receptor (e.g., CCR5 or CXCR4) lead to dissociation of gp120 from gp41 and a cascade of refolding events in the latter (Harrison (2005) *Adv. Virus Res.* 64:231). In the course of these rearrangements, the N-terminal "fusion peptide" of gp41 translocates and inserts into the target cell membrane. A proposed extended conformation of the gp41 ectodomain, with its fusion peptide thus inserted and the transmembrane anchor still in the viral membrane, has been called the "prehairpin intermediate" (Chan and Kim (1998) *Cell* 93:681). The prehairpin intermediate is the target of various fusion inhibitors, including T-20/Enfuvirtide, the first approved fusion-inhibiting antiviral drug (Kilby and Eron (2003) *N. Engl. J. Med.* 348:2228). The characteristics of the intermediate have been deduced from the properties of these inhibitors or mimicries by short gp41 fragments (Eckert et al. *Cell* 99:103; Root et al. (2001) *Science* 291:884). Subsequent rearrangements from the intermediate to the postfusion state of gp41 involve folding back of each of the three chains into a hairpin-like conformation, with two anti-parallel α-helices connected by a disulfide-containing loop. This process brings the fusion peptide and transmembrane anchor, and hence the two membranes, close together at the same end of the refolded protein.

SUMMARY

The present invention is directed in part to the discovery of where, in the sequence of HIV envelope-mediated fusion events, neutralizing antibodies intervene and whether any such antibodies neutralize more than a narrow range of isolates. Biochemically homogeneous forms of the HIV envelope glycoprotein were prepared having defined and uniform antigenic properties. These forms included at least one of each of the principal conformational states of the gp41 ectodomain: the prefusion conformation, the prehairpin intermediate, and the postfusion conformation. The present invention evidences that the epitopes for the MPER antibodies 2F5 and 4E10 are exposed only on a form of the envelope protein designed to mimic an intermediate in the transition from the "prefusion" conformation of the envelope, as found on infectious virions, to the "postfusion" conformation, the final, stable state of gp41 after entry is complete. These results help explain the rarity of 2F5- and 4E10-like antibody responses and indicate how one of skill in the art can design immunogens to elicit them.

Accordingly, in certain exemplary embodiments, an isolated, antigenic polypeptide comprising a prehairpin intermediate conformation of gp41 is provided. The polypeptide includes a first heptad repeat 2 motif, a second heptad repeat 2 motif, a heptad repeat 1 motif, and a membrane-proximal external region. The polypeptide can elicit production of a broadly neutralizing antibody against HIV when injected into a subject. In certain aspects, the polypeptide includes one or more of the following: a C-C loop domain between the second heptad repeat 2 motif and the membrane-proximal external region; a linker between the first heptad repeat 2 motif and the heptad repeat 1 motif; an oligomerization domain (e.g., a trimerization domain) carboxy terminal to the membrane-proximal external region; and a protein tag carboxy terminal to the membrane-proximal external region.

In certain exemplary embodiments, an isolated, antigenic polypeptide comprising a prehairpin intermediate conformation of gp41 is provided having the following order, listed from the amino terminus to the carboxy terminus: a first heptad repeat 2 motif; a heptad repeat 1 motif; a C-C loop domain; a second heptad repeat 2 motif; and a membrane-proximal external region. In certain aspects, the polypeptide elicits production of a broadly neutralizing antibody when injected into a subject.

In certain exemplary embodiments, a vector expressing a polynucleotide encoding a polypeptide comprising a prehairpin intermediate conformation of gp41 is provided. The vector includes the following motifs and domains in the following order (listed from the amino terminus to the carboxy terminus): a first heptad repeat 2 motif; a heptad repeat 1 motif; a C-C loop domain; a second heptad repeat 2 motif; and a membrane-proximal external region.

In certain exemplary embodiments, a method of therapeutically treating a subject infected with HIV is provided. The method includes contacting a subject infected with HIV with a polypeptide comprising an isolated, prehairpin intermediate conformation of gp41 including a first heptad repeat 2 motif, a second heptad repeat 2 motif, a heptad repeat 1 motif and a membrane-proximal external region, and eliciting an immune response in the subject to therapeutically treat the subject. In certain aspects, a broadly neutralizing antibody is produced in the subject. In certain aspects, the HIV titer in the subject infected with HIV is decreased. In other aspects, the HIV is HIV-1. In yet other aspects, HIV infection is eliminated from the HIV-infected subject.

In certain exemplary embodiments, a method of inhibiting an HIV-mediated activity in a subject in need thereof is provided. The method includes contacting an HIV-infected subject with a polypeptide comprising an isolated, prehairpin intermediate conformation of an envelope glycoprotein including a first heptad repeat 2 motif, a second heptad repeat 2 motif, a heptad repeat 1 motif and a membrane-proximal external region to inhibit the HIV-mediated activity. In certain aspects, the HIV-mediated activity is viral spread. In other aspects, HIV titer in the HIV-infected subject is decreased.

In certain exemplary embodiments, a method of preventing HIV infection in a subject including contacting a subject with a polypeptide comprising an isolated, prehairpin intermediate conformation of gp41 including a first heptad repeat 2 motif, a second heptad repeat 2 motif, a heptad repeat 1 motif and a membrane-proximal external region, and eliciting an immune response against the polypeptide in the subject is provided. In certain aspects, a broadly neutralizing antibody against HIV is raised in the subject.

In certain exemplary embodiments, a method of screening a compound that binds to an isolated, prehairpin intermediate conformation of gp41 including providing a polypeptide including an isolated, prehairpin intermediate conformation of gp41 having a first heptad repeat 2 motif, a second heptad repeat 2 motif, a heptad repeat 1 motif and a membrane-proximal external region, contacting the polypeptide with the compound, and determining the ability of the compound to bind to the polypeptide is provided. In certain aspects, the compound inhibits an HIV-mediated activity. In other aspects, the compound is provided in a library.

In certain exemplary embodiments, a vaccine having an epitope comprising an isolated, prehairpin intermediate conformation of gp41 including a first heptad repeat 2 motif, a second heptad repeat 2 motif, a heptad repeat 1 motif and a membrane-proximal external region is provided.

In certain exemplary embodiments, an anti-gp41 antibody specific against an epitope comprising an isolated, prehairpin intermediate conformation of gp41 including a first heptad repeat 2 motif, a second heptad repeat 2 motif, a heptad repeat 1 motif and a membrane-proximal external region is provided.

In certain exemplary embodiments, a method of making an anti-gp41 antibody comprising the steps of providing a host, contacting the host with an epitope comprising an isolated, prehairpin intermediate conformation of gp41 including a first heptad repeat 2 motif, a second heptad repeat 2 motif, a heptad repeat 1 motif and a membrane-proximal external region, and allowing production of an anti-gp41 antibody in the host is provided. In certain aspects, polyclonal antibodies are isolated from the host. In other aspects, a lymphocyte is isolated from the host, and, optionally, a monoclonal antibody is made from the lymphocyte.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

Figure 1:
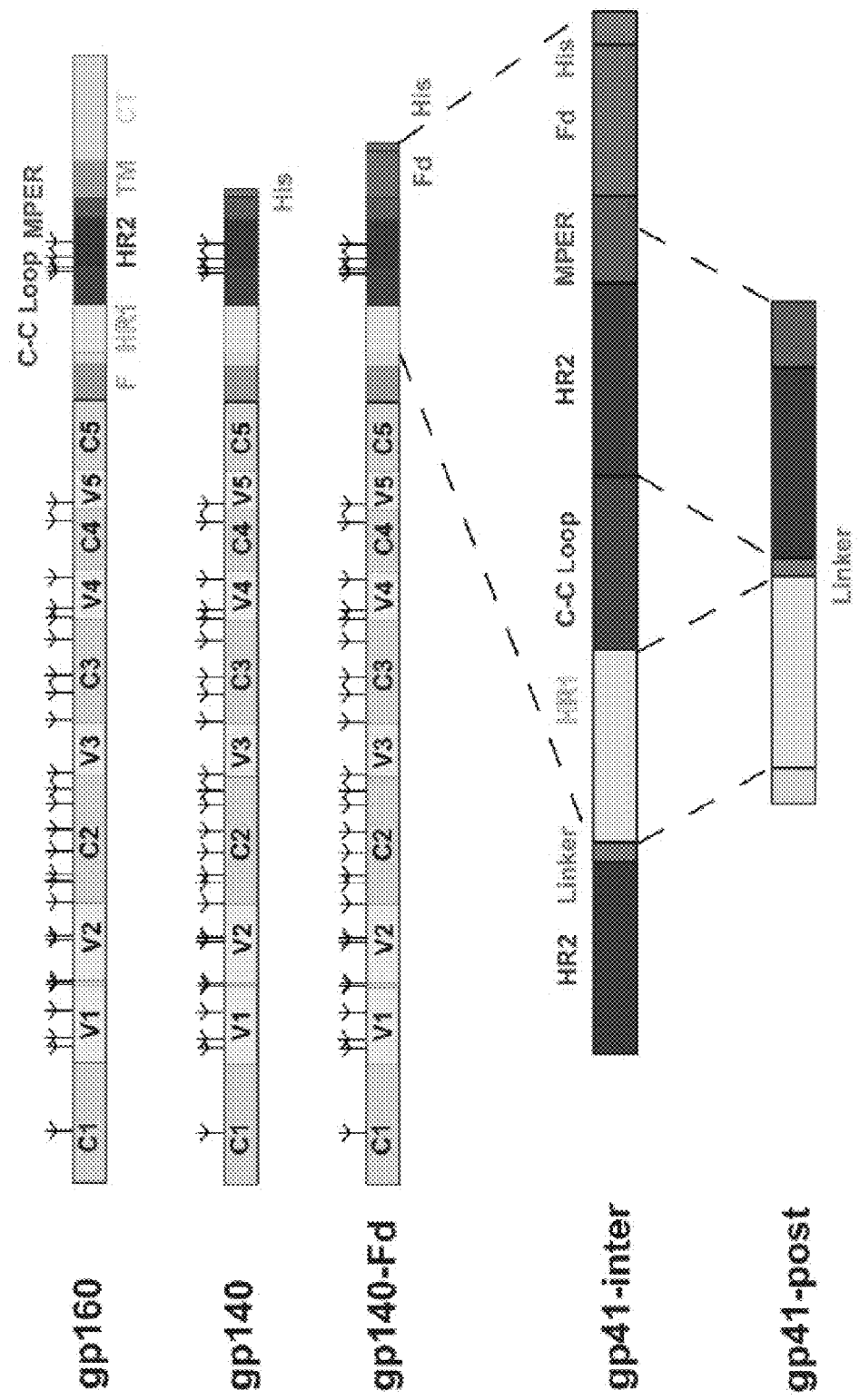
FIG. 1 schematically depicts the design of expression constructs of HIV-1 envelope glycoproteins. Gp160 is the full-length precursor. Various segments of gp120 and gp41 are designated as follows: C1-C5, conserved regions 1-5; V1-V5, variable regions 1-5; F, fusion peptide; HR1, heptad repeat 1; C-C loop, the immunodominant loop with a conserved disulfide bond; HR2, heptad repeat 2; MPER, membrane proximal external region (see FIG. 9); TM, transmembrane anchor; CT, cytoplasmic tail. Expression constructs are: gp140, the uncleaved ectodomain of gp160 with a His-tag at its C-terminus; gp140-Fd, the uncleaved ectodomain of gp160 with a trimerization tag and a His-tag at its C-terminus; gp41-inter, gp41 in the prehairpin intermediate conformation trapped by an N-terminal HR2 peptide- and a C-terminal foldon tag; gp41-post, gp41 in the six helix conformation with partial MPER representing the postfusion state. Glycans are represented by tree-like symbols. At the bottom, diagrams represent the three dimensional organization of these protein species. Gp120 and gp41 in the prefusion state are shown in light green and light blue, respectively. The viral membrane is in orange. Other regions are colored as in the schematics above.
Figure 1:
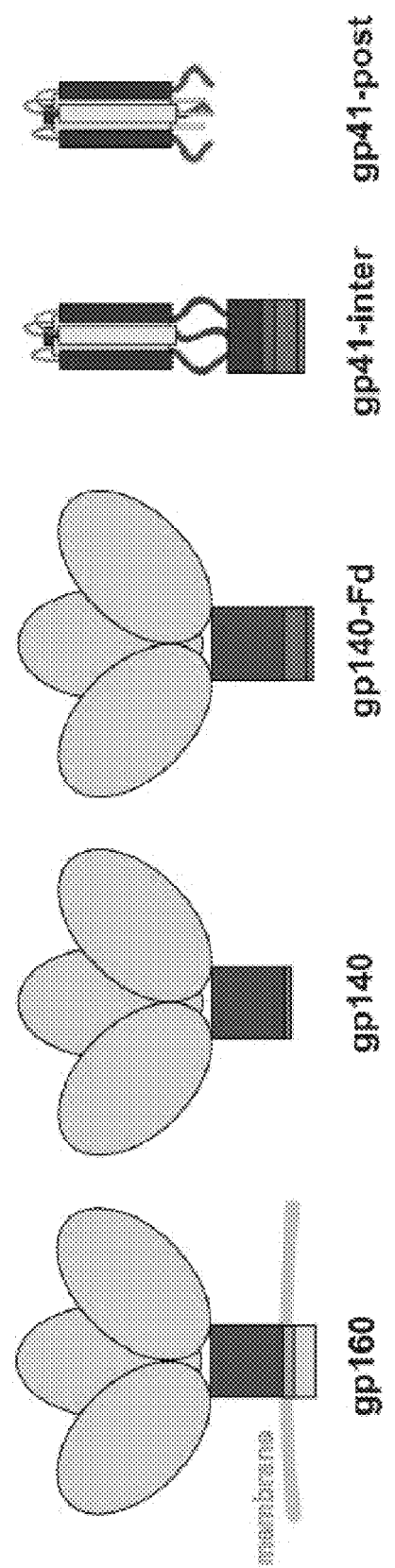

92UGgp140-Fd and 92UGgp41-inter at 1 µM, respectively, were passed over the surface sequentially. No regeneration was needed after the 92UGgp140-Fd binding step. The recorded sensorgram for 92UGgp140-Fd is shown in red and for 92UGgp41-inter in black. (I) The time-course of cleavage of the 92UG-gp140-Fd protein by human plasmin (Sigma) was carried out at room temperature. The first lane on the left is gp140 alone; the last lane on the right is human plasmin alone. Lane 2-9, cleavage proceeded for 5, 10, 15, 20, 30, 60, 90 and 120 minutes. The N-termini of the cleavage products, gp120 and gp41, were confirmed by protein sequencing.

FIGS. 7A-7D depict the characterization of gp41-inter by surface plasmon resonance assay and circular dichroism. (A) Circular dichroism (CD) spectrum of 92UG-gp41-inter. The CD spectrum was recorded at 25° C. with protein concentration of 0.71 µM in PBS. The spectrum was corrected with baseline spectra recorded from buffer alone under the same conditions. (B) The Fab fragment of mAb 2F5 was immobilized on a CM-5 chip. Solutions at various concentrations of HXB2-gp41-inter-GCN4, the gp41-inter protein derived from the HXB2 sequence with a trimeric GCN4 tag, were passed over the chip surface. Binding kinetics were evaluated using BiaEvaluation software (Biocore) and a 1:1 Langmuir binding model. The recorded sensorgrams are shown in black and the fits in green. (C) Two anti-gp41 cluster I antibodies, 240-D or 246-D were immobilized on a CM-5 chip, and, 92UG-gp41-inter-Fd at 1 µM, was passed over the chip surface. The second injection of a duplicate run gave lower binding level because harsh conditions had to be used to regenerate the chip surface and led to lower baseline level. The recorded sensorgrams from the first injection for 240-D and 246-D are shown in black and in blue, respectively. (D) HXB2gp41-interf-GCN4 is not his-tagged and contains the full epitope of 4E10. The his-tagged 4E10 scFv was immobilized to Ni-NTA chip. HXB2gp41-interf-GCN4 at 50 nM was passed over the surface. The recorded sensorgram is shown in black and the fit in green. All injections were carried out in duplicate and gave essentially the same results except in (C). Only one of the duplicates is shown in the figure. Binding constants are summarized in Table 1.

FIGS. 8A-8D depict that mAb 2F5 binds weakly to gp41 in its postfusion conformation. (A) 92UG-gp41-post was expressed from E. coli and extracted from cell pellets by an acid-extraction procedure (see Methods). The protein was purified by HPLC on a C18 column (Vydac) and refolded by a rapid-dilution protocol (see Methods). The refolded protein was concentrated and resolved by gel-filtration chromatography on Superdex 200. The protein migrated on SDS-PAGE as a band of 11 kDa (shown in inset), as expected. (B) Analytical ultracentrifugation was performed on a Beckman XL-A analytical ultracentrifuge at 4° C. Three protein concentrations (0.98, 1.96, 3.92 µM) and three rotor speeds (23000, 28000, 39000 rpm) were used. The data shown were collected with the protein at 3.92 µM and rotor speed of 23000 rpm. Date sets were fitted to a single species model and the molecular weight determined is 34.1+/−0.6 kDa. (C) CD spectrum of 92UG-gp41-post. Circular dichroism (CD) spectrum was recorded at 25° C. with protein concentration of 0.56 mg/ml in PBS. The spectrum was corrected with baseline spectra recorded from buffer alone under the same conditions. (D) The Fab fragment of the broadly neutralizing antibody 2F5 was immobilized on a CM-5 chip. Solutions of 92UG-gp41-post at various concentrations (1.0, 2.5, 5.0 and 10.0 µM) were passed over the chip surface. The recorded sensorgrams are shown in black for 92UG-gp41-post and in green for the fits.

FIG. 9 depicts a sequence alignment of the MPER regions of the constructs used.

Sequences of the membrane-proximal external region from the various constructs and peptides are listed. The 2F5 epitope is highlighted in red and the 4E10 epitope in magenta. Sequence identifiers are as follows: 92UGgp140-Fd is set forth as SEQ ID NO:1; HXB2gp41interf is set forth as SEQ ID NO:2; 92UGgp41inter is set forth as SEQ ID NO:3; 92UGgp41post is set forth as SEQ ID NO:4; 2F5 epitope peptide is set forth as SEQ ID NO:5; and 4E10 epitope peptide is set forth as SEQ ID NO:6.

DETAILED DESCRIPTION

Most antibodies induced by HIV-1 are ineffective at preventing initiation or spread of infection, as they are either non-neutralizing or narrowly isolate-specific. One of the biggest challenges in HIV vaccine development is to design an HIV envelope immunogen that can induce protective, neutralizing antibodies effective against the diverse HIV-1 strains that characterize the global pandemic. Indeed, the generation of "broadly neutralizing" antibodies that recognize relatively conserved regions on the envelope glycoprotein are rare. The present invention is based in part on the stringent characterization of homogeneous preparations of trimeric HIV-1 envelope protein in relevant conformations, followed by the analysis of the molecular mechanism of neutralization by two broadly neutralizing antibodies, 2F5 and 4E10. It was discovered that the epitopes of 2F5 and 4E10 are the membrane-proximal segment of the envelope-protein ectodomain, and that these epitopes are exposed only on a form of the envelope glycoprotein designed to mimic an intermediate state during viral entry. These results explain the rarity of 2F5- and 4E10-like antibody responses and indicate a novel strategy for eliciting broadly neutralizing antibody responses in a host.

Embodiments of the present invention are directed to scaffolds for maintaining an amino acid sequence or protein, such as membrane-proximal external regions, in an immunogenic or antigenic conformation. According to one aspect of the present invention, scaffolds can be altered or designed to maintain the same or a substantially similar amino acid sequence or protein in an immunogenic or antigenic conformation. Different scaffold designs can maintain the same amino acid sequence or protein in an immunogenic or antigenic conformation. In addition, the amino acid sequences or proteins of the present invention can be altered or modified according to methods known in the art to have different sequences yet still be capable of being placed in an immunogenic or antigenic conformation. It is to be understood that the specific amino acid sequences and proteins described herein include sequences and proteins that are substantially similar or homologous thereto or those that can be modified in a manner contemplated by those skilled in the art without departing from the spirit and operation of the invention.

Accordingly, the present invention is directed in part to prehairpin intermediate conformations of the envelope protein (e.g., gp41) of a human immunodeficiency virus (e.g., HIV-1) and methods for their use. In certain exemplary embodiments, the compounds and methods described herein are used to inhibit or decrease one or more HIV-mediated activities (e.g., infection, fusion (e.g., target cell entry and/or syncytia formation), viral spread and the like) in a subject, which can, in turn, decrease HIV titer.

As used herein, the terms "inhibiting" or "decreasing" with respect to HIV refer to an inhibition or decrease of an HIV-mediated activity (e.g., infection, fusion (e.g., target cell entry and/or syncytia formation), viral spread and the like) and/or a decrease in viral titer. For example, an HIV-mediated activity may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more.

HIV is a member of the genus *Lentivirinae*, part of the family of *Retroviridae*. Two species of HIV infect humans: HIV-1 and HIV-2. As used herein, the terms "human immunodeficiency virus" and "HIV" refer, but are not limited to, HIV-1 and HIV-2. In certain exemplary embodiments, the envelope proteins described herein refer to those present on any of the five serogroups of lentiviruses that are recognized: primate (e.g., HIV-1, HIV-2, simian immunodeficiency virus (SIV)); sheep and goat (e.g., visna virus, caprine arthritis encephalitis virus); horse (equine infectious anemia virus); cat (e.g., feline immunodeficiency virus (FIV)); and cattle (e.g., bovine immunodeficiency virus (BIV)) (See International Committee on Taxonomy of Viruses descriptions).

HIV is categorized into multiple clades with a high degree of genetic divergence. As used herein, the term "clade" refers to related human immunodeficiency viruses classified according to their degree of genetic similarity. There are currently three groups of HIV-1 isolates: M, N, and O. Group M (major strains) consists of at least ten clades, A through J. Group O (outer strains) may consist of a similar number of clades. Group N is a new HIV-1 isolate that has not been categorized in either group M or O. In certain exemplary embodiments, a broadly neutralizing antibody described herein will recognize and raise an immune response against two, three, four, five, six, seven, eight, nine, ten or more clades and/or two or more groups of HIV.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into gp120 and gp140. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

In certain exemplary embodiments, a prehairpin intermediate conformation of an HIV envelope glycoprotein is provided. As used herein, the term "prehairpin intermediate conformation" refers, but is not limited to, the form of an envelope glycoprotein, e.g., of gp41, that is present during the transition from the "prefusion" conformation of the envelope glycoprotein, as is found on infectious virions, to the "postfusion" conformation, the final, stable conformation after viral entry into a target cell is complete. In certain aspects, a prehairpin intermediate conformation of an envelope protein includes one, two or more heptad repeat 1 (HR1) motifs, one, two or more heptad repeat 2 (HR2) motifs, and one, two or more membrane-proximal external regions (MPER). In certain optional aspects, a prehairpin intermediate conformation of an envelope protein further includes one or more linker regions. In other optional aspects, a prehairpin intermediate conformation of an envelope protein includes one or more C-C loop domains. In yet other optional aspects, a prehairpin intermediate conformation of an envelope protein includes one or more oligomerization domains. In certain exemplary embodiments, a prehairpin intermediate conformation of an envelope protein includes, listed in amino terminal to carboxy terminal order: HR2-HR1-HR2-MPER. In certain exemplary embodiments, a prehairpin intermediate conformation of an envelope protein includes, listed in amino terminal to carboxy terminal order: HR2-[optional linker]-HR1-HR2-MPER; HR2-HR1-HR2-[optional C-C loop domain]-MPER; HR2-HR1-HR2-MPER-[optional oligomerization domain]; or HR2-HR1-HR2-MPER-[optional protein tag]. In certain aspects, a prehairpin intermediate conformation of an envelope protein includes one, two or more oligomerization domains (e.g., trimerization domains), one, two or more HR2 motifs, and one, two or more MPERs. In certain exemplary embodiments, a prehairpin intermediate conformation of an envelope protein includes, listed in amino terminal to carboxy terminal order: oligomerization domain-HR2-MPER. In certain exemplary embodiments, a prehairpin intermediate conformation of an envelope protein includes, listed in amino terminal to carboxy terminal order: oligomerization domain-[optional C-C loop domain]-HR2-MPER. In certain exemplary embodiments, a prehairpin intermediate conformation of an envelope protein includes, listed in amino terminal to carboxy terminal order: GCN4 trimerization domain-[optional C-C loop domain]-HR2-MPER. In certain exemplary embodiments, a prehairpin intermediate conformation of an envelope protein may contain one, two, three or all four of the one or more optional linkers, optional C-C loop domains, optional oligomerization domains and optional protein tags. In still other exemplary embodiments, a prehairpin intermediate conformation of an envelope protein includes one or more of the specific constructs described further herein (infra).

As used herein, the terms "heptad repeat 1" and "HR1" refer, but are not limited to, a heptad repeat region that is located at the amino terminus of wild-type gp41. As used herein, the terms "heptad repeat 2" and "HR2" refer, but are not limited to, a heptad repeat region that is located at the carboxy terminus of wild-type gp41. A heptad repeat is a motif in which a hydrophobic amino acid is repeated every seven residues; such motifs are designated a through g (Lupas (1996) *Trends Biochem. Sci.* 21:375). Heptad repeats which contain hydrophobic or neutral residues at the a and d positions can form alpha helices and are able to interact with other heptad repeats by forming coiled coils (Chambers et al. (1990) *J. Gen. Virol.* 71:3075; and Lupas, supra). The gp41 HR1 and HR2 sequences are well known in the art and are described in, e.g., Miller et al. (2005) *Proc. Natl. Acad. Sci. USA* 102:14759.

As used herein, the terms "membrane-proximal external region" and "MPER" refer, but are not limited to, a highly conserved region of the gp41 ectodomain adjacent to the viral membrane that is well known in the art.

As used herein, the term "C-C loop domain" refers, but is not limited to, an immunodominant loop present in gp41 proteins that has a conserved disulfide bond. The HIV C-C loop domain is well known in the art.

As used herein, the terms "linker" and "linker region" refer, but are not limited to, a polypeptide sequence used to linearly connect two polypeptide sequences. The linker region may, optionally, add flexibility between the linked polypeptide sequences. A linker region may consist of 5, 10, 15, 20, 25, 30 or more amino acid residues. In certain exemplary embodiments, a linker region comprises serine and glycine residues. In certain exemplary embodiments, a linker region consists of 1, 2, 3, 4, 5, 6, 7, 8, 9 or 10 amino acid residues. In certain exemplary embodiments, a linker region is a short (e.g., less than 10 amino acid residues), flexible connector of serines and glycines.

As used herein, the term "oligomerization domain" refers, but is not limited to, a polypeptide sequence that can be used to increase the stability of an oligomeric envelope protein such as, e.g., to increase the stability of an HIV gp41 trimer.

Oligomerization domains may increase the stability of dimers, trimers, tetramers, pentamers, hexamers, heptamers, octamers, nonamers, decamers and larger oligomers. Oligomerization domains can be used to increase the stability of homooligomeric polypeptides as well as heterooligomeric polypeptides. Oligomerization domains are well known in the art.

As used herein, the terms "trimerization domain" and "trimerization tag" refer to an oligomerization region that stabilizes trimeric polypeptides (e.g., a gp41 homotrimeric polypeptide). Examples of trimerization domain include, but are not limited to, the T4-fibritin "foldon" trimer; the coiled-coil trimer derived from GCN4 (Yang et al. (2002) *J. Virol.* 76:4634); the catalytic subunit of *E. coli* aspartate transcarbamoylase as a trimer tag (Chen et al. (2004) *J. Virol.* 78:4508). Trimerization domains are well known in the art.

As used herein, the term "protein tag" refers, but is not limited to, a polypeptide sequence that can be added to another polypeptide sequence for a variety of purposes. In certain exemplary embodiments, a protein tag may be removed from a larger polypeptide sequence when it is no longer needed. Protein tags include, but are not limited to, affinity tags (e.g., poly-His tags, chitin binding protein (CBP), maltose binding protein (MBP), glutathione-s-transferase (GST) and the like), solubilization tags (e.g., include thioredoxin (TRX), poly(NANP) MBP, GST and the like), chromatography tags (e.g., polyanionic amino acids such as the FLAG epitope), epitope tags (e.g., FLAG-tag, V5-tag, c-myc-tag, HA-tag and the like), fluorescent tags (e.g., green fluorescent protein (GFP), yellow fluorescent protein (YFP), cyan fluorescence protein (CFP) and the like), bioluminescent tags (e.g., luciferase (e.g., bacterial, firefly, click beetle, sea pansy (Renilla) and the like), luciferin, aequorin and the like), enzyme modification tags (e.g., biotin ligase and the like) and the like. Protein tags are well known in the art and their reagents are often commercially available.

In certain exemplary embodiments, a prehairpin intermediate conformation of an envelope glycoprotein described herein can be administered to a subject in whom it is desirable to promote an immune response. In other exemplary embodiments, a nucleic acid sequence encoding one or more prehairpin intermediate conformations of an envelope protein described herein can be administered to a subject in whom it is desirable to promote an immune response.

Accordingly, one or more prehairpin intermediate conformations of envelope glycoprotein(s) can be used as immunogens to produce anti-prehairpin intermediate conformation antibodies in a subject, to inhibit or prevent infection by HIV and/or to inhibit or prevent the spread of HIV in an infected individual. One or more prehairpin intermediate conformations of an envelope glycoprotein described herein can be used as an immunogen to generate antibodies that bind wild-type envelope glycoprotein (i.e., gp41 and/or gp160) using standard techniques for polyclonal and monoclonal antibody preparation.

In certain exemplary embodiments, a prehairpin intermediate conformation of an envelope glycoprotein is capable of eliciting a broadly neutralizing antibody response in a host (including, e.g., one or more of the antibodies described herein (e.g., specific antibodies described in the Examples)). As used herein, the term "broadly neutralizing antibody response" is well known in the art and refers to the ability of one or more antibodies to react with an infectious agent to destroy or greatly reduce the virulence of the infectious agent. The presence of such a response has the potential to prevent the establishment of infection and/or to significantly reduce the number of cells that become infected with HIV, potentially delaying viral spread and allowing for a better control of viral replication in the infected host. A broadly neutralizing antibody against HIV will typically bind a variety of different clades, groups or mutants of HIV.

As used herein, the term "immune response" is intended to include, but is not limited to, T and/or B cell responses, that is, cellular and/or humoral immune responses. The immune response of a subject can be determined by, for example, assaying antibody production, immune cell proliferation, the release of cytokines, the expression of cell surface markers, cytotoxicity, and the like. As used herein, the term "immune cell" is intended to include, but is not limited to, cells that are of hematopoietic origin and play a role in an immune response. Immune cells include, but are not limited to, lymphocytes, such as B cells and T cells; natural killer cells; myeloid cells, such as monocytes, macrophages, eosinophils, mast cells, basophils, and granulocytes.

A prehairpin intermediate conformation of an envelope glycoprotein typically is used to prepare antibodies by immunizing a suitable subject, (e.g., rabbit, goat, mouse or other mammal) with the immunogen. An appropriate immunogenic preparation can contain, for example, a recombinantly expressed prehairpin intermediate conformation of an envelope glycoprotein or a chemically synthesized prehairpin intermediate conformation of an envelope glycoprotein. The preparation can further include an adjuvant, such as Freund's complete or incomplete adjuvant, or similar immunostimulatory agent. Immunization of a suitable subject with an immunogenic prehairpin intermediate conformation of an envelope glycoprotein preparation induces a polyclonal anti-envelope (e.g., anti-gp41 and/or anti-gp160) antibody response, e.g., an anti-HIV antibody response.

Accordingly, in certain exemplary embodiments, anti-prehairpin intermediate conformation of gp41 antibodies are provided. The term "antibody" as used herein refers to immunoglobulin molecules and immunologically active portions of immunoglobulin molecules, i.e., molecules that contain an antigen binding site which specifically binds (immunoreacts with) an antigen, such as the envelope glycoprotein (e.g., gp41 and/or gp160). Examples of immunologically active portions of immunoglobulin molecules include F(ab) and F(ab')2 fragments which can be generated by treating the antibody with an enzyme such as pepsin. The invention provides polyclonal and monoclonal antibodies that bind the envelope glycoprotein (e.g., gp41 and/or gp160). The term "monoclonal antibody" or "monoclonal antibody composition," as used herein, refers to a population of antibody molecules that contain only one species of an antigen binding site capable of immunoreacting with a particular epitope of the envelope glycoprotein (e.g., gp41 and/or gp160). A monoclonal antibody composition thus typically displays a single binding affinity for a particular the envelope glycoprotein (e.g., gp41 and/or gp160) with which it immunoreacts.

Polyclonal anti-envelope glycoprotein (e.g., gp41 and/or gp160) antibodies can be prepared as described above by immunizing a suitable subject with a prehairpin intermediate conformation of an envelope glycoprotein immunogen as described herein. The anti-prehairpin intermediate conformation of an envelope glycoprotein antibody titer in the immunized subject can be monitored over time by standard techniques, such as with an enzyme linked immunosorbent assay (ELISA) using immobilized gp41. If desired, the antibody molecules directed against gp41 can be isolated from the mammal (e.g., from the blood) and further purified by well known techniques, such as protein A chromatography to obtain the IgG fraction. At an appropriate time after immunization, e.g., when the anti-gp41 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with a prehairpin intermediate conformation of an envelope glycoprotein immunogen as described above, and the culture supernatants of the resulting hybridoma cells are screened to identify a hybridoma producing a monoclonal antibody that binds gp41.

Any of the many well known protocols used for fusing lymphocytes and immortalized cell lines can be applied for the purpose of generating an anti-prehairpin intermediate conformation of an envelope glycoprotein monoclonal antibody (see, e.g., G. Galfre et al. (1977) *Nature* 266:55052; Gefter et al. *Somatic Cell Genet*., cited supra; Lerner, *Yale J. Biol. Med*. (supra); Kenneth, *Monoclonal Antibodies*, (supra)). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Particularly suitable immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of a prehairpin intermediate conformation of an envelope glycoprotein are detected by screening the hybridoma culture supernatants for antibodies that bind gp41, e.g., using a standard ELISA assay.

Alternative to preparing monoclonal antibody-secreting hybridomas, a monoclonal anti-prehairpin intermediate conformation of an envelope glycoprotein antibody can be identified and isolated by screening a recombinant combinatorial immunoglobulin library (e.g., an antibody phage display library) with a gp41 protein to thereby isolate immunoglobulin library members that bind gp41. Kits for generating and screening phage display libraries are commercially available (e.g., Recombinant Phage Antibody System, Pfizer, New York, N.Y.; and the SURFZAP™ Phage Display Kit, Stratagene, La Jolla, Calif.). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352: 624-628; Gram et al. (1992) *Proc. Natl. Acad. Sci. USA* 89:3576-3580; Garrad et al. (1991) *Bio/Technology* 9:1373-1377; Hoogenboom et al. (1991) *Nucl. Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-prehairpin intermediate conformations of envelope glycoprotein antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In certain exemplary embodiments, antibodies, fusion inhibiting agents (e.g., small molecules, peptides and the like) and the like that are capable of interacting with a prehairpin intermediate conformation of an HIV envelope glycoprotein are provided. As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in *Molecular Biology of the Cell,* 3d edition, Garland Publishing, 1994. Steric interactions are generally understood to include those where the structure of the compound is such that it is capable of occupying a site by virtue of its three dimensional structure, as opposed to any attractive forces between the compound and the site.

In certain exemplary embodiments, compositions and methods for enhancing the immune response of a subject to a human immunodeficiency virus are provided. As used herein, the terms "subject" and "host" are intended to include living organisms such as mammals. Examples of subjects and hosts include, but are not limited to, horses, cows, sheep, pigs, goats, dogs, cats, rabbits, guinea pigs, rats, mice, gerbils, non-human primates (e.g., macaques), humans and the like, non-mammals, including, e.g., non-mammalian vertebrates, such as birds (e.g., chickens or ducks) fish or frogs (e.g., *Xenopus*), and non-mammalian invertebrates, as well as transgenic species thereof.

In certain exemplary embodiments, vectors such as, for example, expression vectors, containing a nucleic acid encoding one or more prehairpin intermediate conformations of an envelope protein described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more prehairpin intermediate conformations of an envelope protein described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more prehairpin intermediate conformations of an envelope protein is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., one or more prehairpin intermediate conformations of an envelope protein).

In certain exemplary embodiments, nucleic acid molecules described herein can be inserted into vectors and used as gene therapy vectors. Gene therapy vectors can be delivered to a subject by, for example, intravenous injection, local administration (see, e.g., U.S. Pat. No. 5,328,470), or by stereotactic injection (see, e.g., Chen et al. (1994) *Proc. Natl. Acad. Sci. U.S.A.* 91:3054). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, adeno-associated virus vectors, and the like, the pharmaceutical preparation can include one or more cells which produce the gene delivery system (See Gardlik et al. (2005) *Med. Sci. Mon.* 11:110; Salmons and Gunsberg (1993) *Hu. Gene Ther.* 4:129; and Wang et al. (2005) *J. Virol.* 79:10999 for reviews of gene therapy vectors).

Recombinant expression vectors of the invention can be designed for expression of one or more encoding one or more prehairpin intermediate conformations of an envelope protein in prokaryotic or eukaryotic cells. For example, one or more vectors encoding one or more prehairpin intermediate conformations of an envelope protein can be expressed in bacterial cells such as *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40); pMAL (New England Biolabs, Beverly, Mass.); and pRIT5 (Pharmacia, Piscataway, N.J.) which fuse glutathione S-transferase (GST), maltose E binding protein, or protein A, respectively, to the target recombinant protein.

In another embodiment, the expression vector encoding one or more prehairpin intermediate conformations of an envelope protein is a yeast expression vector. Examples of vectors for expression in yeast *S. cerevisiae* include pYepSec1 (Baldari, et. al., (1987) *EMBO J.* 6:229-234); pMFa (Kurjan and Herskowitz, (1982) *Cell* 30:933-943); pJRY88 (Schultz et al., (1987) *Gene* 54:113-123); pYES2 (Invitrogen Corporation, San Diego, Calif.); and picZ (Invitrogen Corporation).

Alternatively, one or more prehairpin intermediate conformations of an envelope protein can be expressed in insect cells using baculovirus expression vectors. Baculovirus vectors available for expression of proteins in cultured insect cells (e.g., Sf9 cells) include the pAc series (Smith et al. (1983) *Mol. Cell. Biol.* 3:2156-2165) and the pVL series (Lucklow and Summers (1989) *Virology* 170:31-39).

In certain exemplary embodiments, a nucleic acid described herein is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, adenovirus 2, cytomegalovirus and simian virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235), in particular promoters of T cell receptors (Winoto and Baltimore (1989) *EMBO J.* 8:729) and immunoglobulins (Banerji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. U.S.A.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374) and the α-fetoprotein promoter (Campes and Tilghman (1989) *Genes Dev.* 3:537).

In certain exemplary embodiments, host cells into which a recombinant expression vector of the invention has been introduced are provided. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more prehairpin intermediate conformations of an envelope protein can be expressed in bacterial cells such as *E. coli*, viral cells such as retroviral cells, insect cells, yeast or mammalian cells (such as Chinese hamster ovary cells (CHO) or COS cells). Other suitable host cells are known to those skilled in the art.

Delivery of nucleic acids described herein (e.g., vector DNA) can be by any suitable method in the art. For example, delivery may be by injection, gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI® (Polyplus-transfection Inc., New York, N.Y.), EFFECTENE® (Qiagen, Valencia, Calif.), DREAMFECT® (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Embodiments of the invention are directed to a first nucleic acid (e.g., a nucleic acid sequence encoding one or more gp41 domains or motifs such as, for example, HR1 from a wild type gp41 strain, HR2 from a wild type gp41 strain, MPER from a wild type gp41 strain and the like) or polypeptide sequence (e.g., one or more gp41 domains or motifs such as, for example, HR1 from a wild type gp41 strain, HR2 from a wild type gp41 strain, MPER from a wild type gp41 strain and the like) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.* 14:6745. An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule.

A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

A first polynucleotide is "derived from" a second polynucleotide if it has the same or substantially the same base-pair sequence as a region of the second polynucleotide, its cDNA, complements thereof, or if it displays sequence identity as described above. A first polypeptide is derived from a second polypeptide if it is encoded by a first polynucleotide derived from a second polynucleotide, or displays sequence identity to the second polypeptides as described above. In the present invention, when a gp41 protein is "derived from HIV" the gp41 protein need not be explicitly produced by the virus itself, the virus is simply considered to be the original source of the gp41 protein and/or nucleic acid sequences that encode it. Gp41 proteins can, for example, be produced recombinantly or synthetically, by methods known in the art, or alternatively, gp41 proteins may be purified from HIV-infected cell cultures.

In certain exemplary embodiments screening assays for identifying modulators, i.e., candidate or test compounds or agents (e.g., antibodies, peptides, cyclic peptides, peptidomimetics, small molecules, small organic molecules, or other drugs) which have an inhibitory effect on gp41 and/or one or more HIV mediated activities described herein (e.g., one or more prehairpin intermediate conformations of an envelope protein) are provided.

As used herein, the term "small molecule" refers to a molecule, either naturally occurring or synthetic, that has a molecular weight of more than about 25 daltons and less than about 3000 daltons, usually less than about 2500 daltons, more usually less than about 2000 daltons, usually between about 100 to about 1000 daltons, more usually between about 200 to about 500 daltons.

In certain exemplary embodiments, assays for screening candidate or test compounds which bind to or modulate (e.g., inhibit) one or more prehairpin intermediate conformations of an envelope protein are provided. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

The test compound(s), antibodies, one or more prehairpin intermediate conformations of an envelope protein and/or nucleic acid sequences encoding one or more prehairpin intermediate conformations of an envelope protein described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the test compound(s), one or more antibodies, one or more prehairpin intermediate conformations of an envelope protein and/or nucleic acid sequences encoding one or more prehairpin intermediate conformations of an envelope protein described herein in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the test compound(s), one or more antibodies, one or more prehairpin intermediate conformations of an envelope protein and/or nucleic acid sequences encoding one or more prehairpin intermediate conformations of an envelope protein described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The test compound(s), one or more antibodies, one or more prehairpin intermediate conformations of an envelope protein and/or nucleic acid sequences encoding one or more prehairpin intermediate conformations of an envelope protein described herein can also be prepared in the form of suppositories (e.g., with conventional suppository bases such as cocoa butter and other glycerides) or retention enemas for rectal delivery.

In one embodiment, the test compound(s), one or more antibodies, one or more prehairpin intermediate conformations of an envelope protein and/or nucleic acid sequences encoding one or more one or more prehairpin intermediate conformations of an envelope protein described herein are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of the test compound(s), one or more antibodies, one or more prehairpin intermediate conformations of an envelope protein and/or nucleic acid sequences encoding one or more one or more prehairpin intermediate conformations of an envelope protein described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of a viral infection, e.g., HIV infection, includes the step of administering a therapeutically effective amount of an agent (e.g., one or more test compounds, one or more antibodies, one or more prehairpin intermediate conformations of an envelope protein, a nucleic acid sequence that encodes one or more prehairpin intermediate conformations of an envelope protein and the like) which modulates (e.g., inhibits), one or more envelope protein (e.g., gp41) activities (e.g., mediating viral fusion (e.g., viral entry and/or syncytia formation)) to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, table, and accompanying claims.

Example 1

Stable Conformations of HIV Envelope Glycoprotein

Gp140 Trimer

Figure 2:
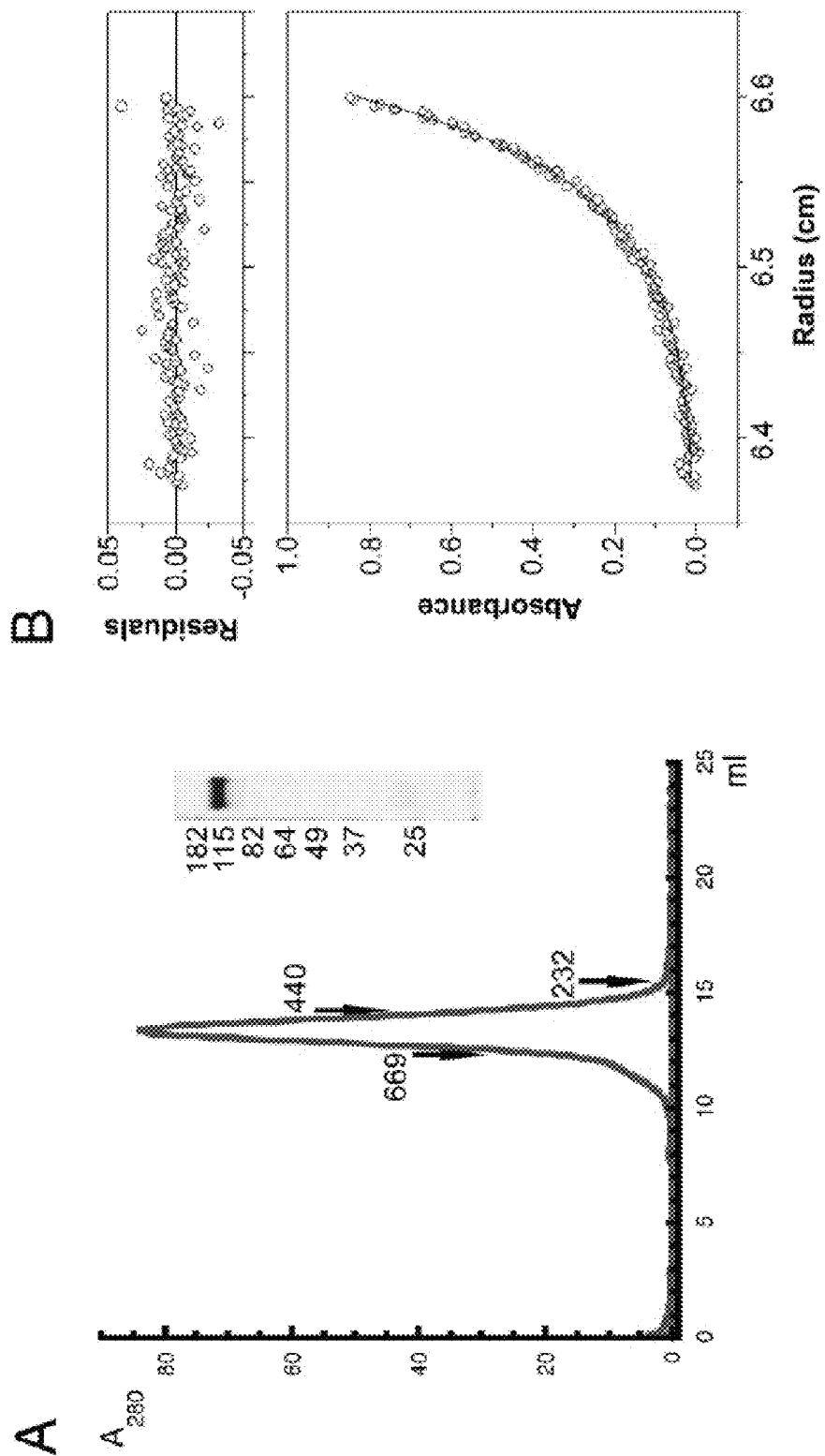
FIGS. 2A-2F depict protein preparations of the prefusion and the pre-hairpin intermediate conformations of HIV-1 gp41. (A) Purified HIV-1 92UG-gp140-Fd trimer was resolved by gel-filtration chromatography using a Superose 6 column. The apparent molecular mass was calculated based on a standard curve using the following known standards: thyoglobulin (670 kDa), ferritin (440 kDa) and catalase (232 kDa). Peak fractions were pooled and analyzed by Coomassie stained SDS-PAGE (inset). (B) Analytical ultracentrifugation for 92UG-gp140-Fd trimer was performed on a Beckman XL-A analytical ultracentrifuge at 4° C. Three protein concentrations (0.62, 1.24, 2.48 µM) and three rotor speeds (5000, 7000, 9000 rpm) were used. The data shown were collected with the protein at 1.24 µM and rotor speed of 7000 rpm. Data sets were fitted to a single species model and the protein partial specific volume was calculated to be 0.686 ml/g based on the sugar content (Laue et al. (1992) in *Analytical Ultracentrifugation in Biochemistry and Polymer Science*, ed. S. E. Harding AJRaJCH (Royal Society of Chemistry, Cambridge), pp. 90-125). The molecular mass determined was 409+/−10 kDa. (C) 92UG-gp140-Fd trimer was treated with various concentrations (lanes 1 to 7, 0, 0.05, 0.25, 0.5, 1, 2, 5 mM, respectively) of EGS (ethylene glycol bis(succinimidylsuccinate)). The crosslinked products were analyzed by SDS-PAGE in a 4% gel. The molecular weight standard was cross-linked phosphorylase b (Sigma). The dimeric and trimeric species of 92UG-gp140-Fd migrate faster than expected for their molecular weights, probably due to their compactness after cross-linking (D) 92UG-gp41-inter was expressed from *E. coli* and refolded in vitro. The refolded protein was resolved by gel-filtration chromatography on Superdex 200. The protein migrated on SDS-PAGE as a band of 26 kDa when sample was boiled and reduced. When not boiled and not reduced, the protein migrated as a ladder of three bands of 26, 50, 80 kDa, respectively, corresponding to monomer, dimer and trimer (shown in inset, lane 1 and 2). (E) Analytical ultracentrifugation for 92UG-gp41-inter was performed on a Beckman XL-A analytical ultracentrifuge at 4° C. Three protein concentrations (0.98, 1.96, 3.92 µM) and three rotor speeds (15000, 17500, 26000 rpm) were used. The data shown were collected with the protein at 3.92 μM and rotor speed of 17500 rpm. Data sets were fitted to a single species model and the molecular weight determined was 92+/−6 kDa. (F) 92UG-gp41-inter examined by negative-stain electron microscopy. A view of a raw image is shown. The bottom row shows selected images after class averaging to increase the signal-to-noise ratio. The dimensions of the rod-like molecules are roughly 150 Å×45 Å. The bar represents 20 nm.
Figure 2:
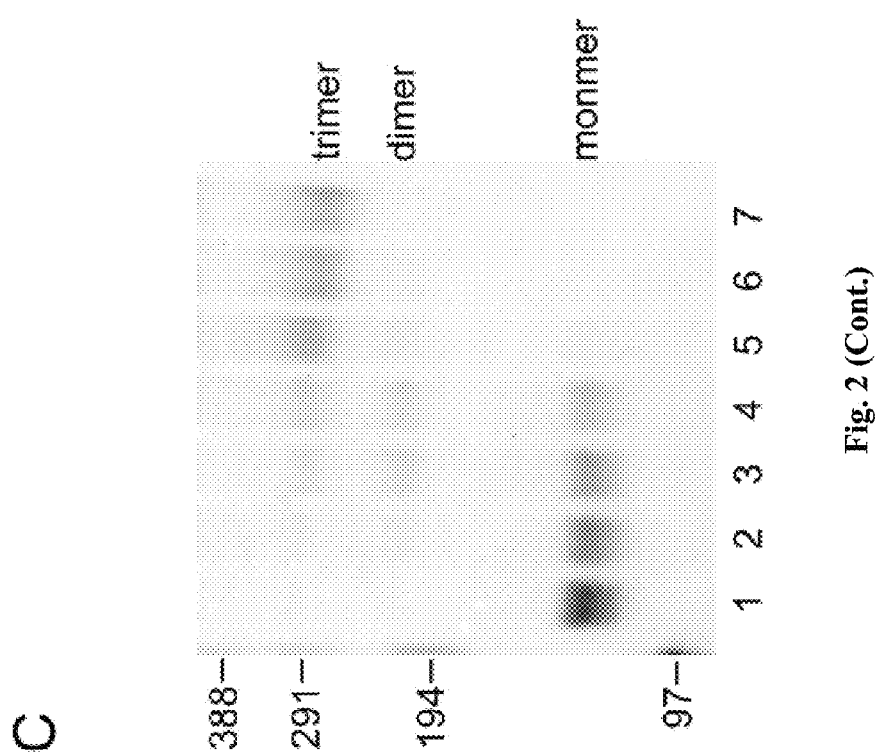
Figure 2:
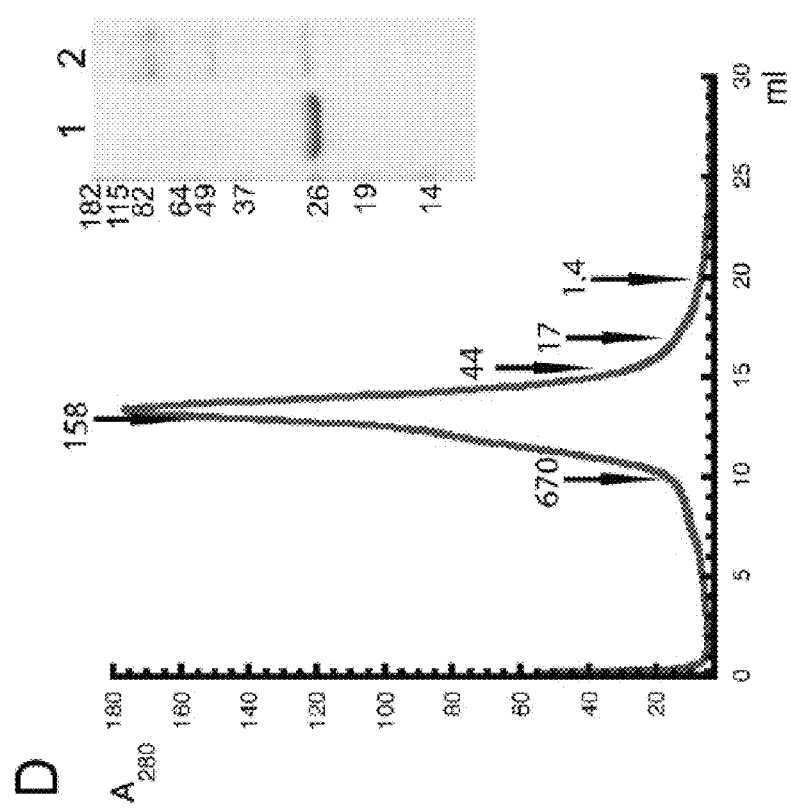
Figure 2:
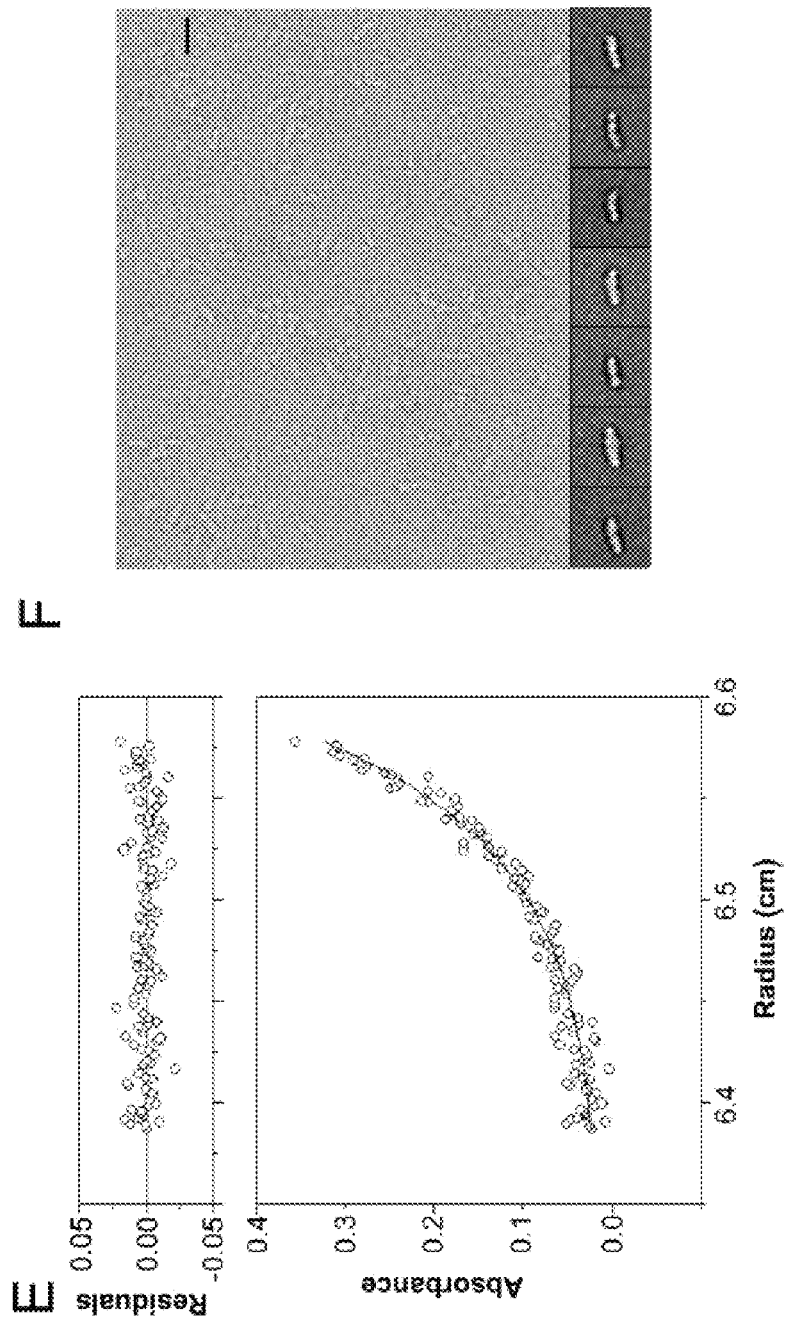
Figure 5:
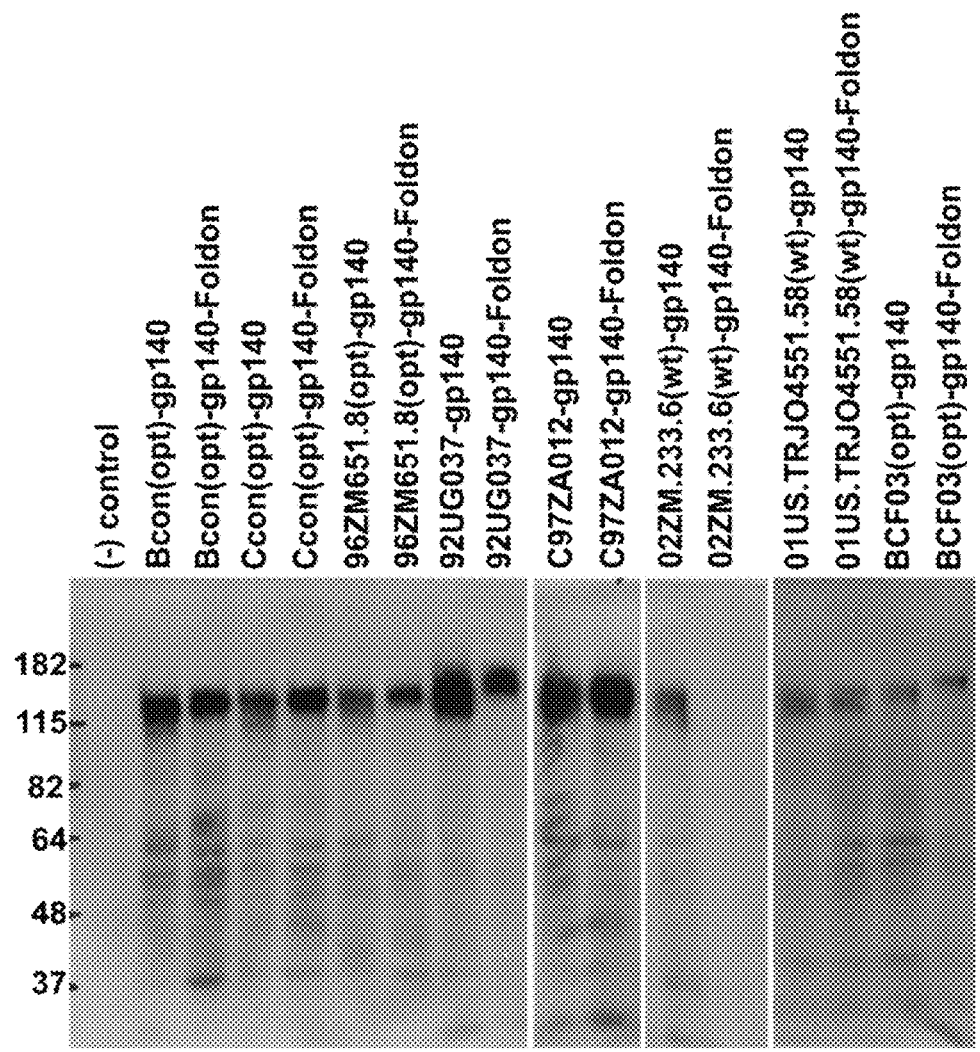
FIG. 5 depicts expression of HIV-1 gp140 in insect cells. HIV-1 gp140 from a series of isolates were expressed in two formats, with or without a foldon trimerization tag at the C-terminus (e.g. gp140 and gp140-Foldon). The HIV-1 strains shown here include Bcon, the consensus sequence of Glade B; Ccon, the consensus sequence of Glade C; 96ZM651.8, a Glade B sequence from chronic infection; 92UG037.8, a Glade A sequence; C97ZA012, a Glade C sequence; 02ZM.233M.6, a Glade C sequence from early infection; 01US.TRJO4551.58, a Glade B sequence from acute infection; and BCF03, a group O sequence. Sf9 cells were infected with the corresponding baculovirus vectors, and cell supernatants were harvested three days post-infection. Each protein contained a six histidine tag at its C-terminus. The secreted gp140 protein was analyzed by SDS-PAGE and immunoblotting with an anti-His-tag antibody. There was no obvious correlation for secretion level, which, without intending to be bound by scientific theory, presumably corresponds to protein stability.

Gp140, the ectodomain of the precursor gp160, is often produced to mimic the prefusion state of the envelope, based on structural studies of related other viral fusion proteins, such as, e.g., influenza hemagglutinin (Skehel and Wiley D C (2000) *Ann. Rev. of Biochem.* 69). However, the stability of HIV-1 gp140 varies greatly from strain to strain and can be enhanced by adding a C-terminal trimerization tag such as the T4-fibritin "foldon" or the coiled-coil trimer derived from GCN4 (Yang et al. (2002) *J. Virol.* 76:4634). Recombinant SIV gp140 is a stable trimer even without such a tag (Chen et al. (2000) *J. Biol. Chem.* 275:34946). Gp140 proteins from a number of HIV-1 primary isolates were expressed with and without trimer tags to identify sequences that yield particularly stable gp140 trimers (FIG. 5). The construct 92UG-gp140-Fd was derived from isolate 92UG037.8 and stabilized by a C-terminal foldon tag. This construct proved to be especially well behaved (FIG. 1). Its properties, analyzed by size-exclusion chromatography, sedimentation equilibrium and chemical cross-linking, are shown in FIG. 2. Uncleaved gp140 from the same isolate but without the C-terminal foldon also yielded a stable trimer, but the foldon form was easier to purify because of its higher affinity for Ni-NTA. To mimic even more closely the conformation of (gp120/gp41)$_3$ on the virion surface, partially cleaved gp140 was generated using human plasmin (FIG. 6I and (Binley et al. (2002) *J. Virol.* 76:2606)), as recombinant furin is very ineffective in vitro.

Gp41-Prehairpin Intermediate

To biochemically produce homogeneous forms of additional conformations, two constructs were designed to capture gp41 in the extended, prehairpin intermediate conformation. As shown in FIG. 1, gp41-inter has the following sequence: (HR2)-linker-[HR1-CC loop-HR2-MPER]-(trimerization tag), where HR1 and HR2 are the first and second heptad repeat motifs found in gp41 from wild type HIV (the segments that form helices in the postfusion trimer of hairpins) and the sequence in brackets is essentially the complete gp41 ectodomain, except for the fusion peptide. The "linker" is a short, flexible connector of serines and glycines. Without intending to be bound by scientific theory, when gp41-inter chains trimerize, it was expected that the N-terminal HR2 segments would form a six-helix bundle with the HR1 segments, and the C-terminal HR2 segments, constrained by the trimerization tag, would be unable to do so. The conformation of this construct could be pictured as the prehairpin intermediate captured by an HR2 peptide, such as T-20. Gp41-inter was expressed using sequences from two isolates: 92UG037.8 and HXB2, with foldon and trimeric GCN4, respectively. In both cases, the protein could be expressed in *E. coli* and refolded in vitro. Control experiments showed that the N-terminal HR2 segment was required for refolding of bacterially expressed protein as well as for obtaining soluble, secreted protein from insect cells. A similar construct with the gp41 sequence of SIVmac32H and the catalytic subunit of *E. coli* aspartate transcarbamoylase as a trimer tag (Chen et al. (2004) *J. Virol.* 78:4508) could likewise be obtained as secreted protein from insect cells, indicating that the overall design is robust and independent of the choice of a C-terminal trimerizing element.

Figure 7:
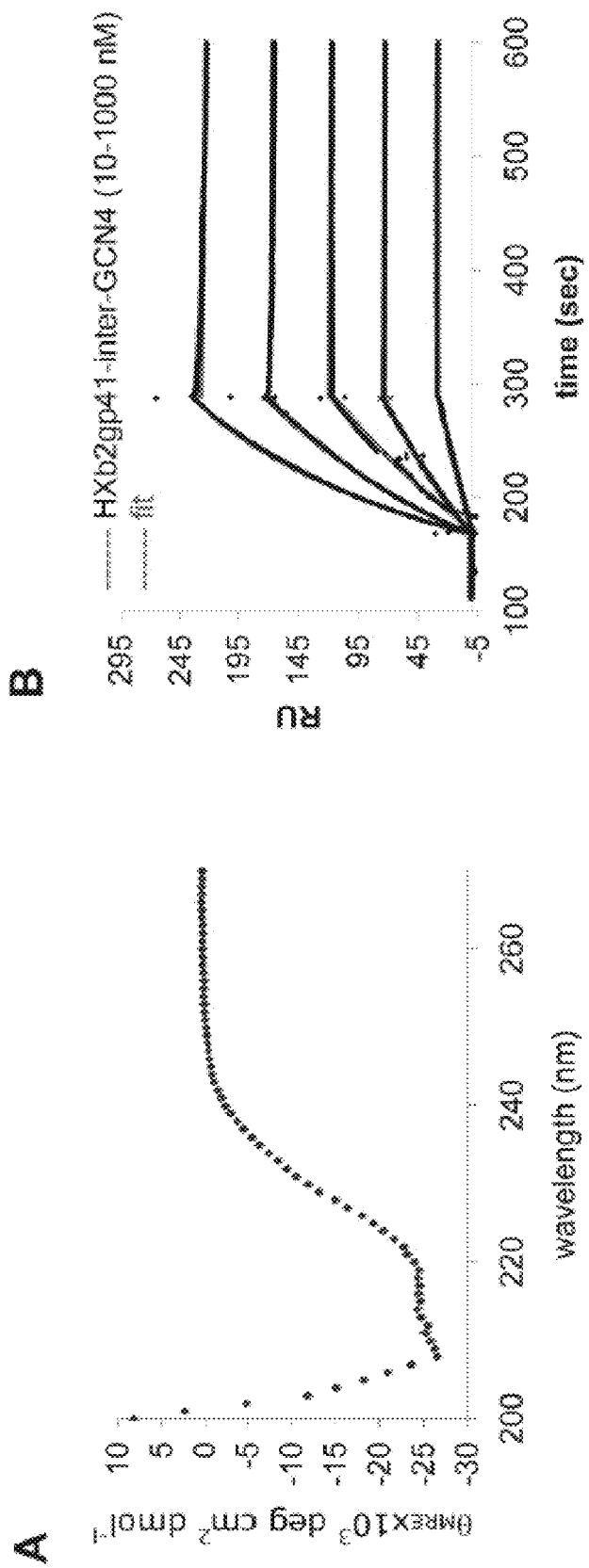
Figure 7:
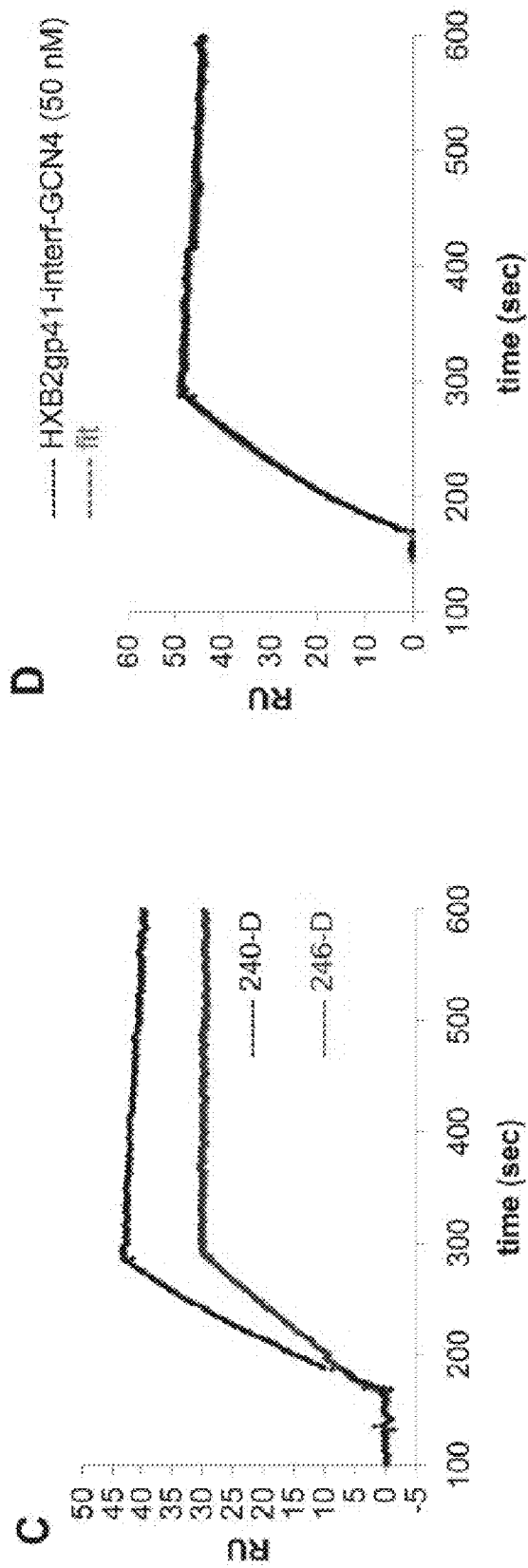

Purified 92UG-gp41-inter was a monodisperse trimer (FIGS. 2D, E), stable even after multiple rounds of gel-filtration chromatography. Its CD spectrum indicated a mixture of secondary structures (FIG. 7A). Negative-stain electron microscopy showed rod-like particles, 150 Å in length and about 45 Å wide (FIG. 2F). The expected lengths for the N-terminal six-helix bundle and the C-terminal foldon are 75 and 28 Å, respectively. Without intending to be bound by scientific theory, the intervening segment of about 100 residues (C-C loop, HR2, and MPER) must have a relatively compact fold, to span just 45 to 50 Å of axial distance. The dry volume of three fully compact chains of this size would be about 35,000 Å$^3$; the volume of an enclosing cylinder, 45 Å in diameter and 50 Å long, is about 75,000 Å$^3$, compatible with normal levels of hydration for a folded protein.

Gp41 Postfusion Six-Helix Bundle

Figure 8:
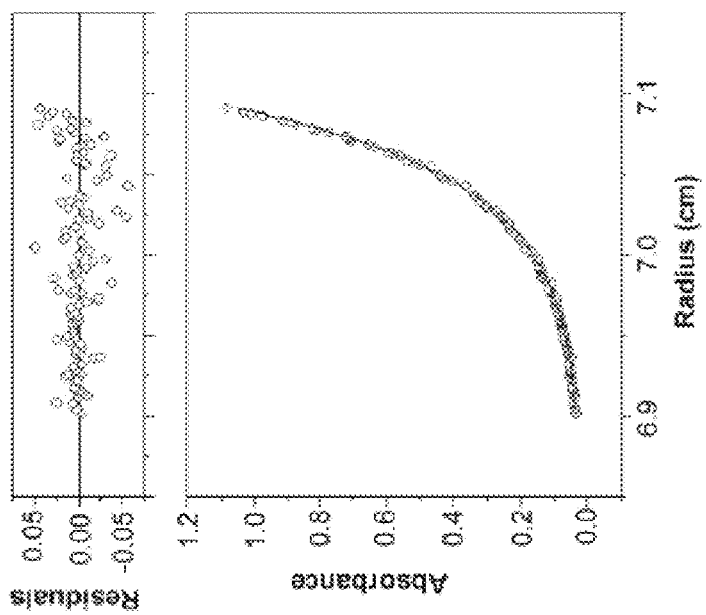
Figure 8:
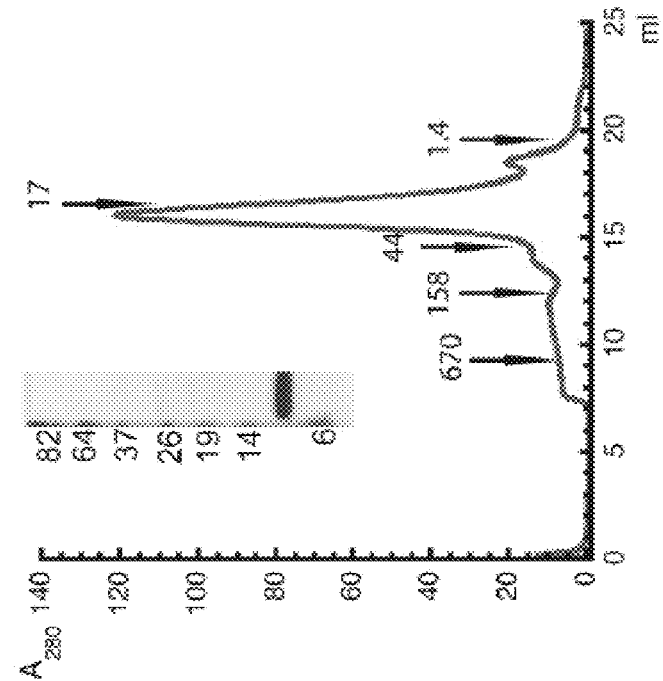
Figure 8:
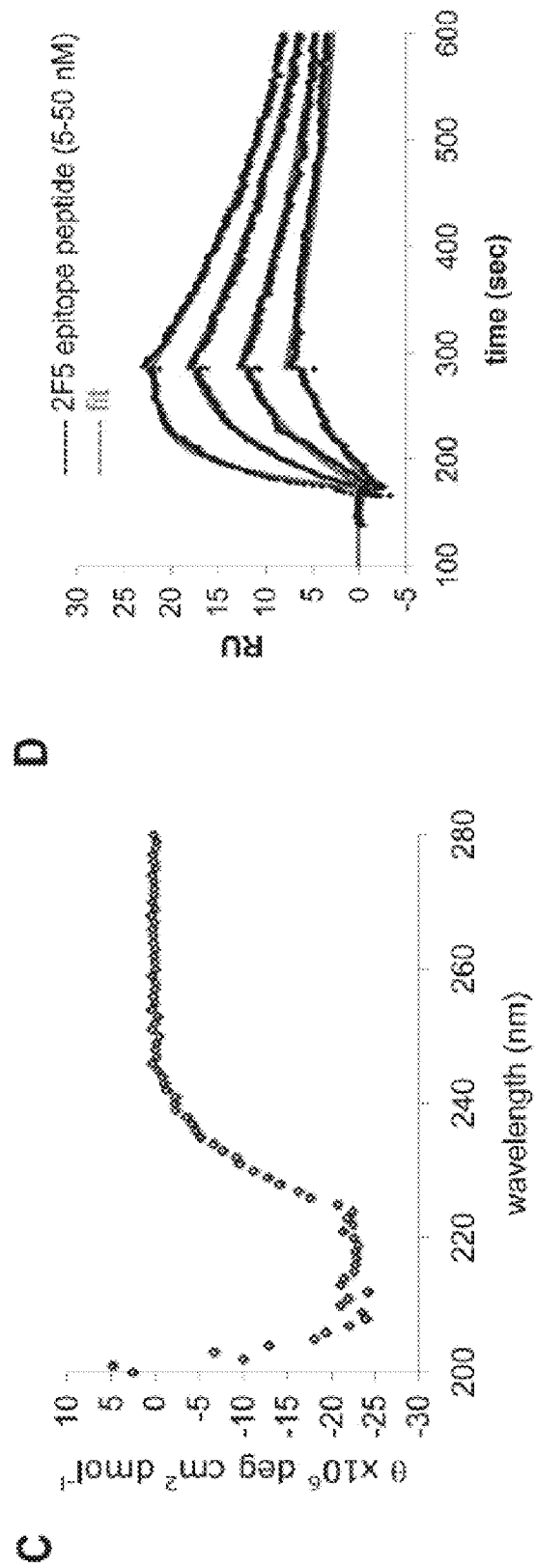

Forms of postfusion gp41 that contained the complete MPER tended to aggregate. A six-helix bundle construct that contained the full 2F5 epitope (LDKWANL) (SEQ ID NO:14), but lacking the 4E10 epitope was prepared (i.e., "gp41-post" (FIG. 1)). As refolded from *E. coli*-expressed inclusion bodies, gp41-post had all the properties expected for a trimer of α-helical hairpins (FIG. 8).

Example 2

Figure 6:
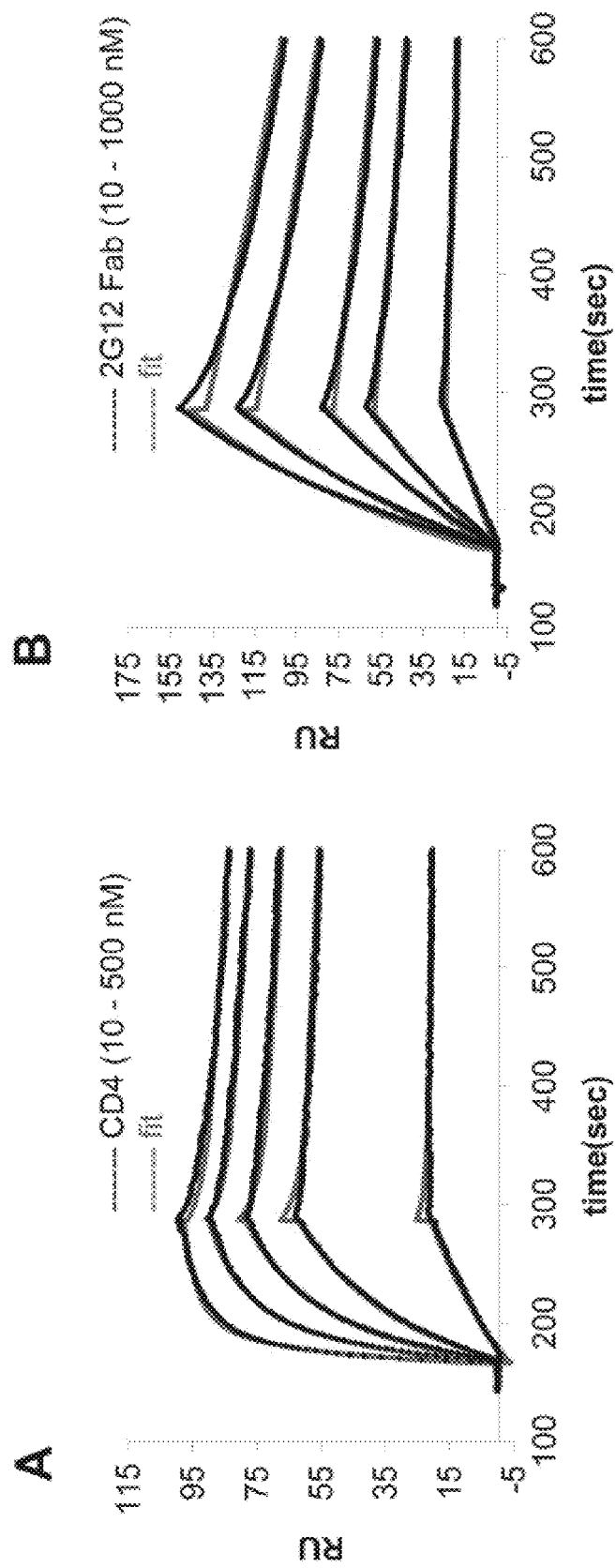
FIGS. 6A-6I depict characterization of the 92UGgp140-Fd trimer. (A) and (B) 92UGgp140-Fd trimer was immobilized on a CM-5 chip, and soluble four-domain CD4 (in A) and the Fab fragment of broadly neutralizing antibody 2G12 (in B) at various concentrations were passed over the chip surface. Binding kinetics was evaluated using BiaEvaluation software (Biacore) using a two-step binding model for CD4 and a 1:1 Langmuir binding model for 2G12. The recorded sensorgrams are shown in black and the fits in green. Binding constants are summarized in Table 1. (C) Monomeric 92UG-gp120 core protein at 1 μM and trimeric 92UG-gp140-Fd protein at 1 μM, respectively, were flowed over a CM-5 chip surface coated with the whole IgG of mAb b12. The recorded sensorgram for 92UG-gp120 core is shown in black and the fit in green. The single curve was fit to a 1:1 Langmuir binding model as published (Rits-Volloch et al. (2006) *Embo J.* 25:5026). The sensorgram of 92UGgp140-Fd trimer is in red. (D) and (E) Monomeric 92UG-gp120 core protein at 0.2 μM (in D) and 1 μM (in E), and trimeric 92UG-gp140-Fd protein at 1 μM, respectively, were flowed over a CM-5 chip surfaces coated with the whole IgG of mAb b6 (in D) and mAb 15e (in E). The recorded sensorgram for 92UG-gp120 core is shown in black and the fit in green. The single curve was fit to a 1:1 Langmuir binding model. The sensorgram of 92UGgp140-Fd trimer is in red. (F) Trimeric 92UG-gp140-Fd protein alone (0.5 μM), soluble CD4 alone (5 μM) and a pre-incubated complex with 0.5 μM of 92UG-gp140-Fd protein and 5 μM of soluble CD4 were passed over a mAb 17b surface on a CM-5 chip. The recorded sensorgram for CD4 alone is shown in black, for 92UGgp140-Fd in blue and for the complex in red. (G) Two anti-gp41 cluster I antibodies, 240-D or 246-D, were immobilized on a CM-5 chip, and 92UG-gp140-Fd trimer at 1 μM, was passed over the chip surface. The recorded sensorgram for 240-D and 246-D are shown in black and in blue, respectively. All injections were carried out in duplicate and gave essentially the same results. Only one of the duplicates is shown in the figure. (H) Immobilization of 4E10 antibody to a CM5 chip directly by the standard amine coupling procedure results in blocking binding to its antigens. To generate a functional 4E10 surface to further confirm binding results derived from using 4E10 antigens as immobilized ligands, purified protein A (Calbiochem) was immobilized to a CM5 chip first and 4E10 IgG was allowed to bind to the surface.
Figure 6:
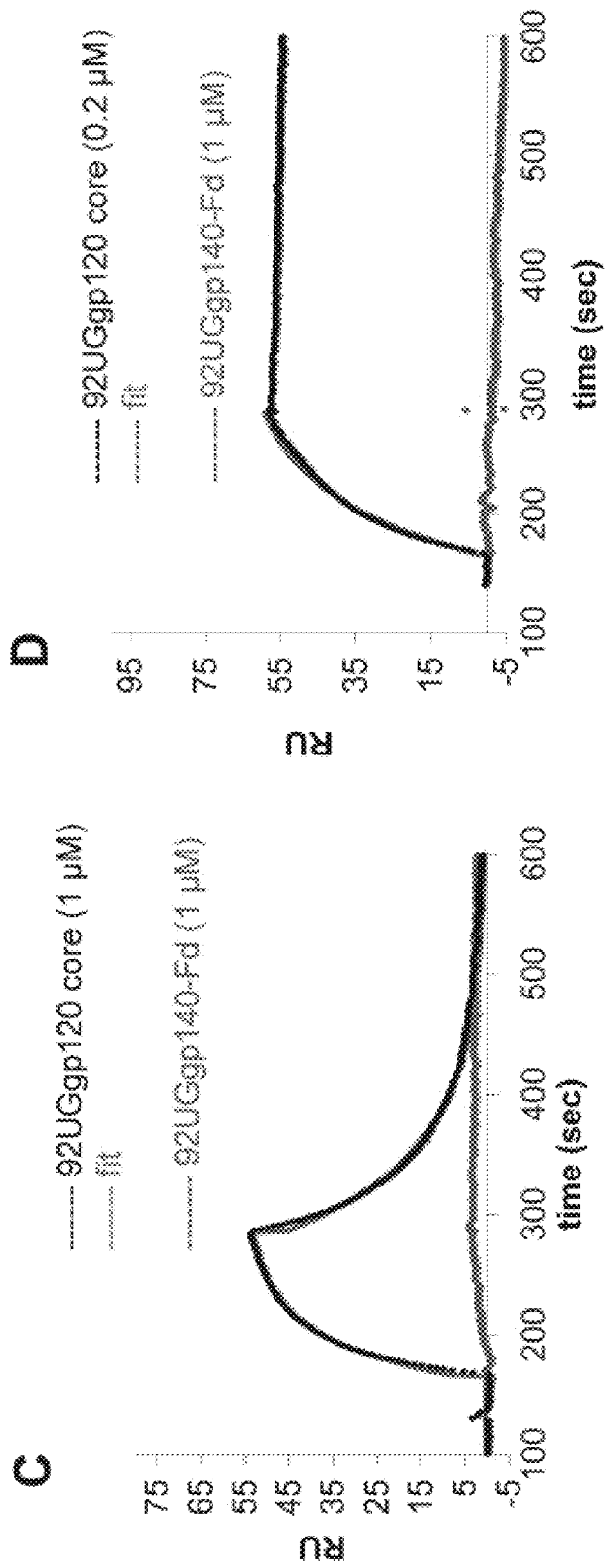
Figure 6:
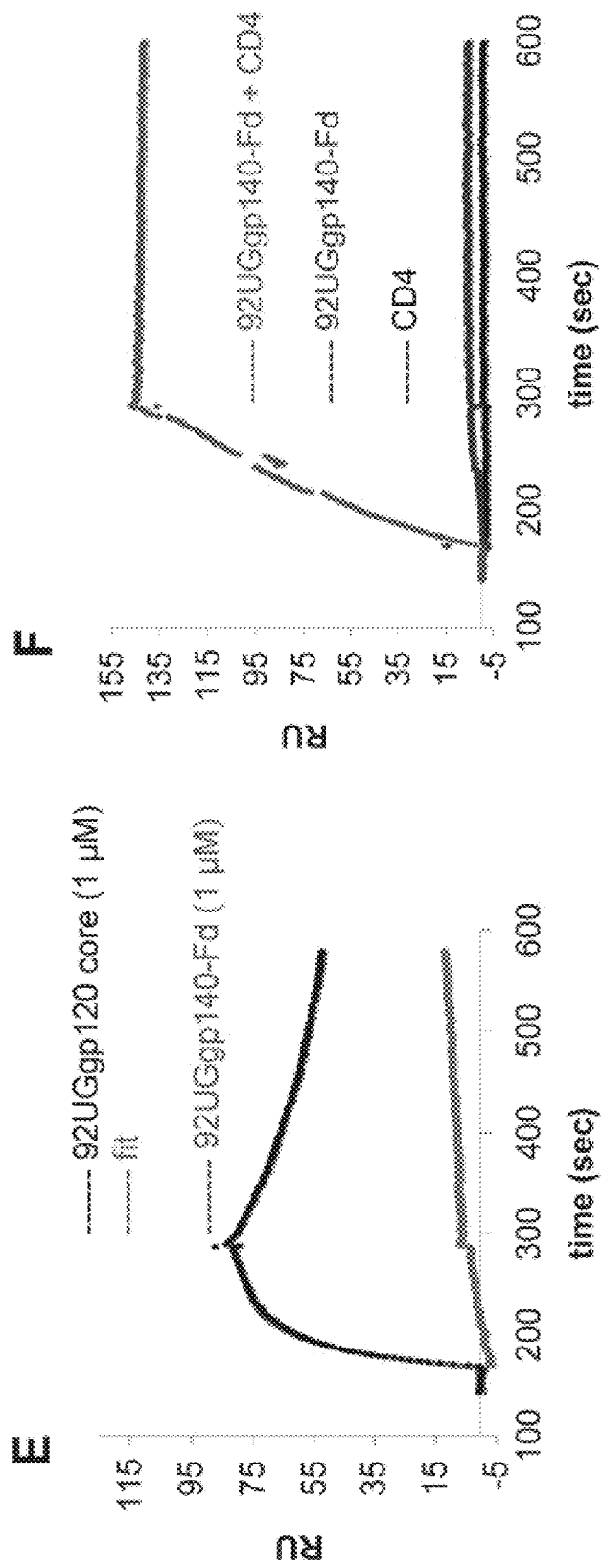
Figure 6:
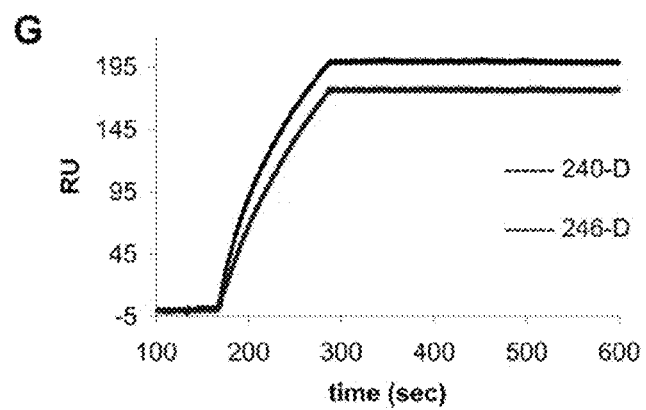
Figure 6:
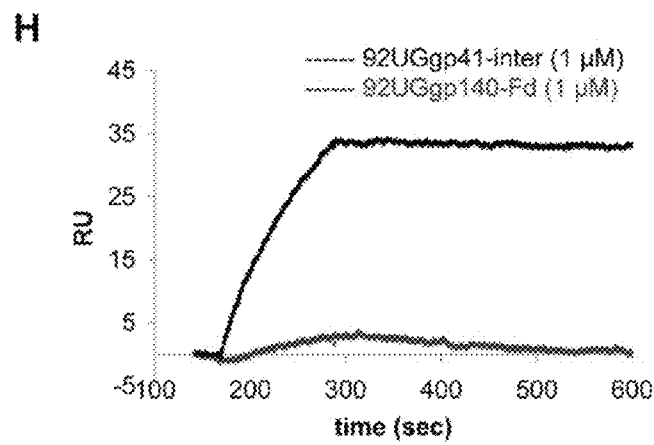
Figure 6:
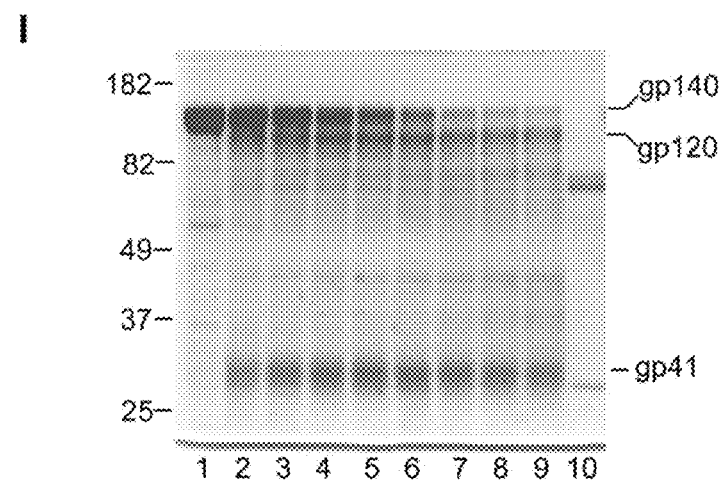

Ligand Binding and Antigenic Properties of Envelope Protein in Distinct Conformational States A series of binding experiments were performed to verify the integrity of the 92UG-gp140-Fd trimer and to analyze its antigenic properties. The 92UG-gp140-Fd trimer bound CD4 with a $K_d$ of 1.98 nM (Table 1 and FIG. 6A); the surface-plasmon-resonance (SPR) sensorgrams were fit using a two-step binding model as used for binding of CD4 to gp120 core (Rits-Volloch et al. (2006) *Embo J.* 25:5026). Thus, the covalent linkage between gp120 and gp41 did not impede the conformational change in gp120 that accompanies CD4 binding. The 92UG-gp140-Fd trimer also bound mAb 2G12 (Trkola et al. (1996) *J. Virol.* 70:1100) with high affinity (Table 1 and FIG. 6B) as expected, since the 92UG037 isolate was sensitive to neutralization by 2G12 (Binley et al. (2004) *J. Virol.* 78:13232). The trimer failed to bind the b12 IgG (Burton et al. (1994) *Science* 266:1024), consistent with the resistance of the isolate to neutralization by that mAb (Binley et al. (2004) *J. Virol.* 78:13232), but the monomeric gp120 derived from 92UG037 did bind b12, with a $K_d$ of 1.4 μM (Rits-Volloch et al. (2006) *Embo J.* 25:5026; and FIG. 6C). This affinity is about two orders of magnitude weaker than measured for the same mAb with gp120 from isolates HXB2 or YU2 (Zhou et al. (2007) *Nature* 445:732). Without intending to be bound by scientific theory, this is likely due to a sequence difference in the CD4 binding loop (P369L (using HXB2 numbering), a residue that makes direct contact with b12 (Id.)). In addition, the 92UG-gp140-Fd trimer did not bind two other non-neutralizing CD4 binding site antibodies, b6 and 15e, despite of the high affinities of these two antibodies to 92UG-gp120 core (Table 1; FIGS. 6D and 6E). Without intending to be bound by scientific theory, it was concluded that the position and orientation of gp120 in the prefusion trimer reduced accessibility of the CD4 site to antibodies without impeding accessibility to CD4. Uncleaved 92UG-gp140-Fd also bound a CD41 (CD4-induced) mAb, 17b (Thali et al. (1993) *J. Virol.* 67:3978), but only in the presence of CD4, as expected (FIG. 6F). This result indicated that the gp120 part of this trimer could undergo the conformational transition associated with formation of the bridging sheet, the docking site for mAb 17b (and for co-receptor), even when gp120 could not fully dissociate, consistent with the similar observations from other groups (Yang et al. (2002) *J. Virol.* 76:4634).

Table 1 depicts binding rate constants derived from SPR analysis. [a]These binding constants were derived by fitting the sensorgram with a single concentration of analyte. The results presented here for b12 IgG are essentially identical to those published previously by fitting runs with multiple concentrations (Chen et al. (2004) *J. Virol.* 78:4508). [b]These sensorgrams are virtually flat during the dissociation phase, making accurate fitting very difficult. Thus, without intending to be bound by scientific theory, the actual off-rates are probably even slower than those listed here. [c]The short 2F5 epitope peptide used was ELLELDKWASL (SEQ ID NO:15). [d]The 4E10 epitope peptide was biotin-SLWNWFNITNWLWYIK (SEQ ID NO:16) (Alam et al. (2007) *J. Immunol.* 178:4424)

Antibodies to gp41 include those in "cluster I," which bind the immunodominant, disulfide-containing loop between the two helical regions of the postfusion form, and those in "cluster II," which bind MPER epitopes. The 92UG-gp140-Fd trimer bound tightly with two cluster I mAbs, 240-D and 246-D (FIG. 6G), in accord with earlier observations that SIV gp140 trimer interacts with cluster I mAbs, KK41 and 9G3, and that the cluster I epitopes are well-exposed on the primary HIV-1 native virions (Xu et al. (1991) *J. Virol.* 65:4832; Kim et al. (2001) *J. Biol. Chem.* 276:42667; Nyambi et al. (2000) *J. Virol.* 74:7096). We note that mAb 9G3 has neutralizing activity (Kim et al. (2001) *J. Biol. Chem.* 276:42667). We also find strong binding of 240-D and 246-D with plasmin-cleaved 92UG-gp140-Fd, but as the cleavage is incomplete, one cannot make strong conclusions about the effects of gp120-gp41 cleavage on antibody affinity. Some previous reports suggest that cluster I and II epitopes are exposed on uncleaved, oligomeric gp140 but inaccessible on cleaved, disulfide-linked, monomeric SOS gp140 derived from the same strain (Schulke et al. (2002) *J. Virol.* 76:7760). The conformational homogeneity of those preparations was not fully assessed, and the cluster I epitope in the SOS gp140 was also altered by the extra disulfide introduced.

The 92UG037 isolate was sensitive to neutralization by the broadly neutralizing, MPER-directed human monoclonal antibodies, 2F5 and 4E10 (Binley et al. (2004) *J. Virol.* 78:13232), and these two antibodies indeed recognized

TABLE 1

Figure 3:
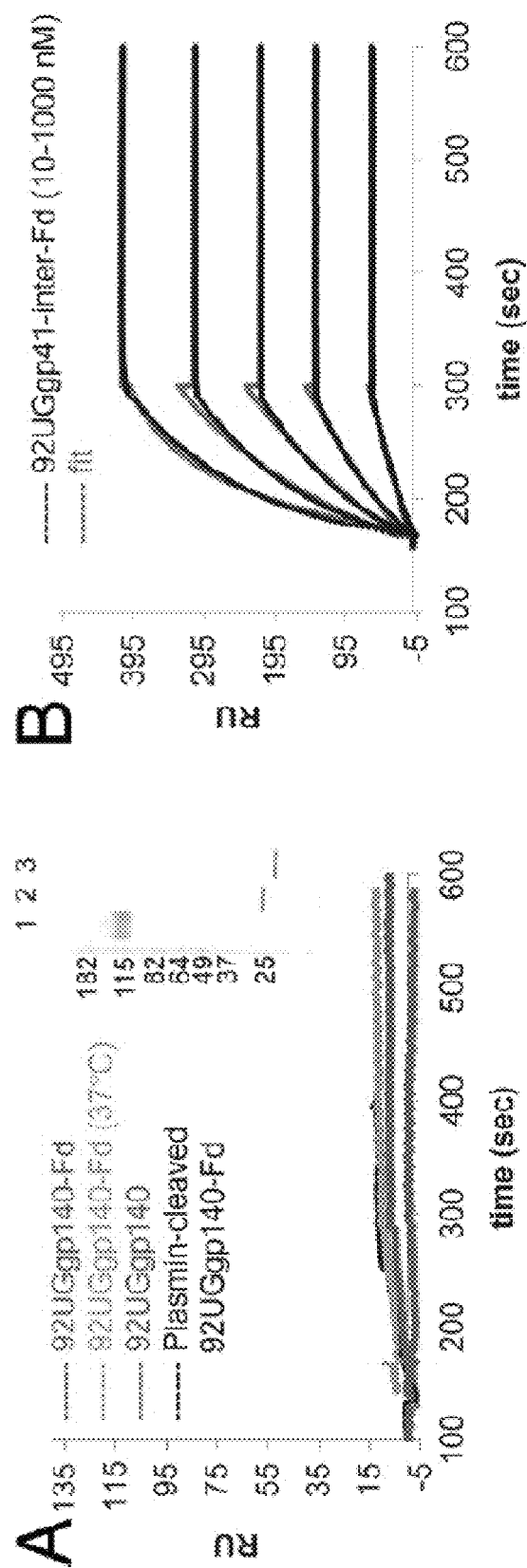
FIGS. 3A-3D depict evidence that the broadly neutralizing mAb 2F5 targets the prehairpin intermediate conformation. (A) 2F5 Fab was immobilized on a CM-5 chip, and 92UG-gp140-Fd (1 μM) or 92UG-gp140 (without Foldon tag, 1 μM) were passed over the surface. The sensorgram for 92UG-gp140-Fd is shown in pink, 92UG-gp140-Fd at 37° C. in orange and 92UG-gp140 in red. The 92UG-gp140-Fd was cleaved by human plasmin, and the cleaved gp140-Fd was further purified away from aggregated protein and plasmin by gel-filtration chromatography on a prep-grade Superdex 200 column. The peak fraction containing cleaved, trimeric gp140-Fd was immobilized on a Ni-NTA chip, and 2F5 Fab at 1 μM was passed over the surface. The sensorgram for partially cleaved gp140-Fd is shown in black. No binding of 2F5 to any of the gp140 proteins was observed. As shown in the inset, 2F5 did react on an immunoblot with 92UG-gp140-Fd (lane 1), as well as the two gp41 proteins in the prehairpin intermediate conformation, 92UG-gp41-inter-Fd (lane 2) and HXB2-gp41-inter-GCN4 (lane 3). (B) The Fab fragment of mAb 2F5 was immobilized on a CM-5 chip. Solutions at various concentrations of 92UG-gp41-inter-Fd, the gp41-inter protein derived from the 92UG037.8 sequence with a foldon tag were passed over the chip surface. Binding kinetics were evaluated using BiaEvaluation software (Biocore) and a 1:1 Langmuir binding model. The recorded sensorgrams are shown in black and the fits in green. (C) The Fab fragment of 2F5 was immobilized on a CM-5 chip. Solutions of 92UG-gp41-post at various concentrations (1.0, 2.5, 5.0 and 10.0 μM) were passed over the chip surface. The recorded sensorgrams are shown in black for 92UG-gp41-post and in green for the fits. (D) T20 peptide at different concentrations (5, 10, 25 and 50 nM) was passed over a surface of a chip bearing immobilized 2F5 Fab. The recorded sensorgrams are shown in black and the fits in green. All injections were carried out in duplicate and gave essentially the same results. Only one of the duplicates is shown in the figure.
Figure 3:
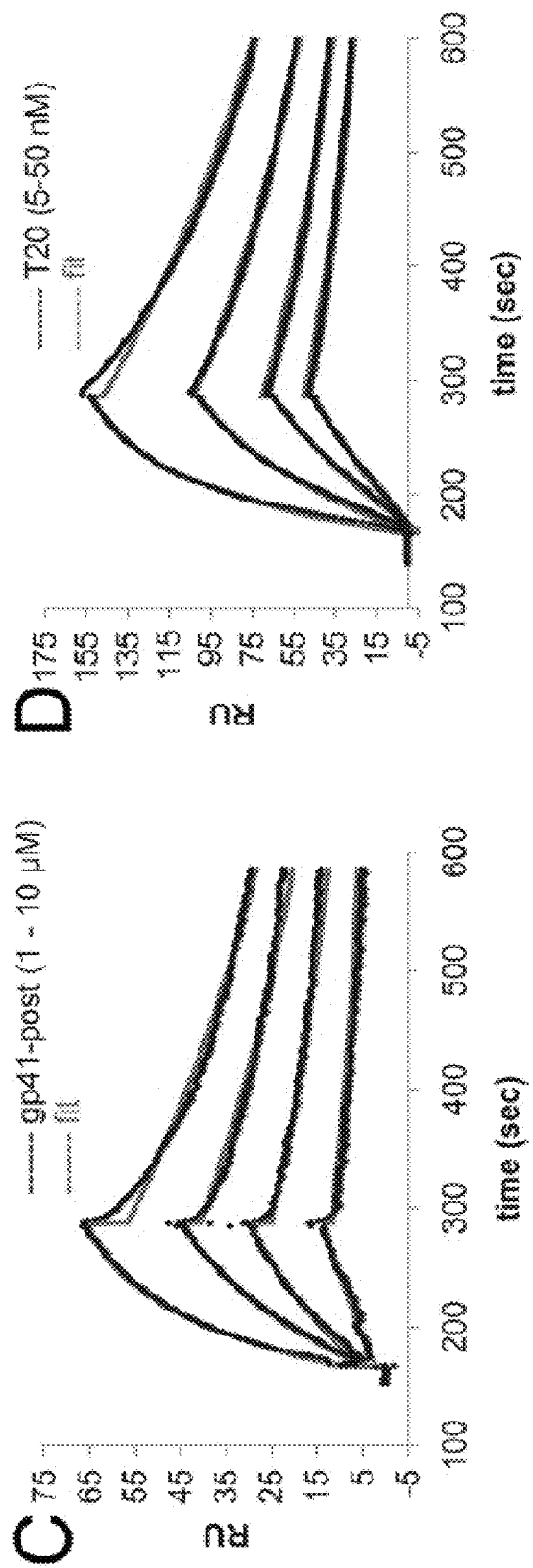
Figure 4:
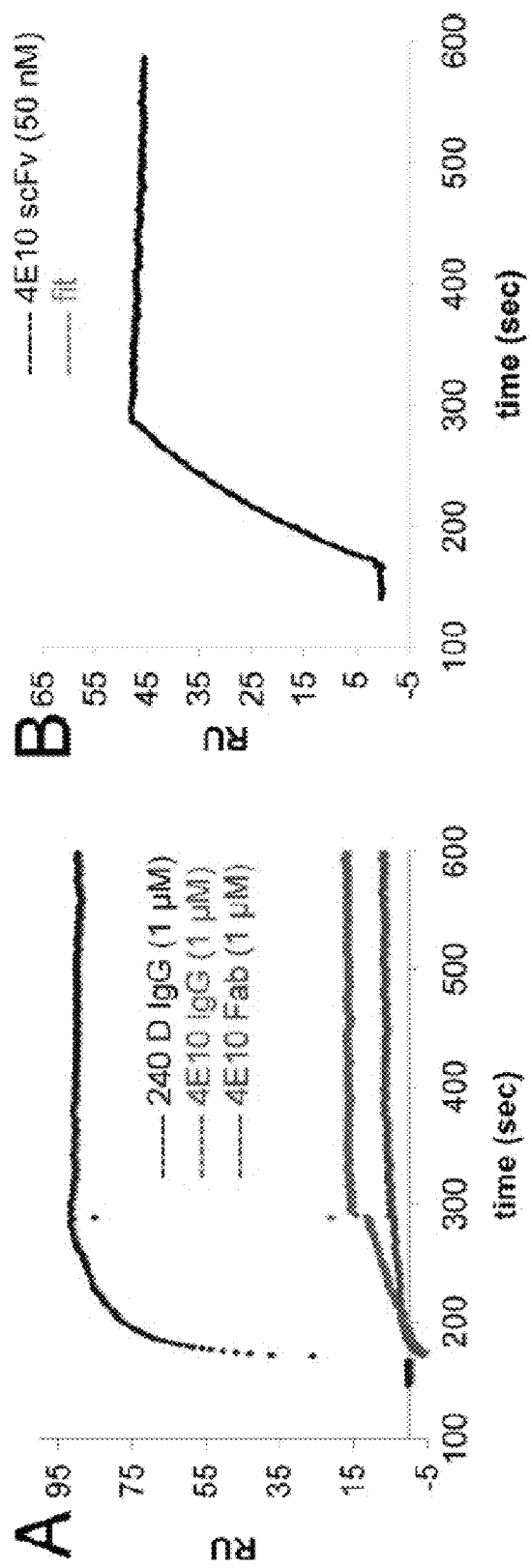
FIGS. 4A-4D depict that the mAb 4E10 also targets the prehairpin intermediate conformation of gp41. (A) To preserve its native conformation, 92UG-gp140-Fd trimer was immobilized on a Ni-NTA chip, and 4E10 IgG, 4E10 Fab and 240-D IgG, all at 1 μM, were passed over the surface sequentially. Regeneration was not necessary after binding by 4E10 IgG and Fab. The recorded sensorgrams are shown in blue for 240-D, in pink for 4E10 IgG and in red for 4E10 Fab. The IgG of 4E10 showed only very weak binding, even with a potential avidity effect. (B) The 92UG-gp41-inter protein was immobilized on a CM-5 chip. A solution of 4E10 scFv at 50 nM was passed over the chip surface. Second injection of a duplicate run gave lower binding level because harsh conditions had to be used to regenerate the chip surface and led to lower baseline level. The experiment was repeated using a different chip and gave the similar result. The recorded sensorgrams are shown in black for 4E10 scFv and in green for the fit. (C) Western blot of 92UG-gp140-Fd trimer and 92UG-gp41-inter detected by mAb 4E10. Both proteins reacted with mAb 4E10, as shown in lane 1 for 92UG-gp140-Fd, and lane 2 for 92UG-gp41-inter (lane 2). (D) Solutions of 4E10 scFv at various concentrations (25-500 nM) were passed over the surface of an SA chip bearing immobilized biotinylated 4E10 epitope peptide. The recorded sensorgrams are shown in black and the fits in green. All injections were carried out in duplicate and gave essentially the same results except in B. Only one of the duplicates is shown in the figure.
Figure 4:
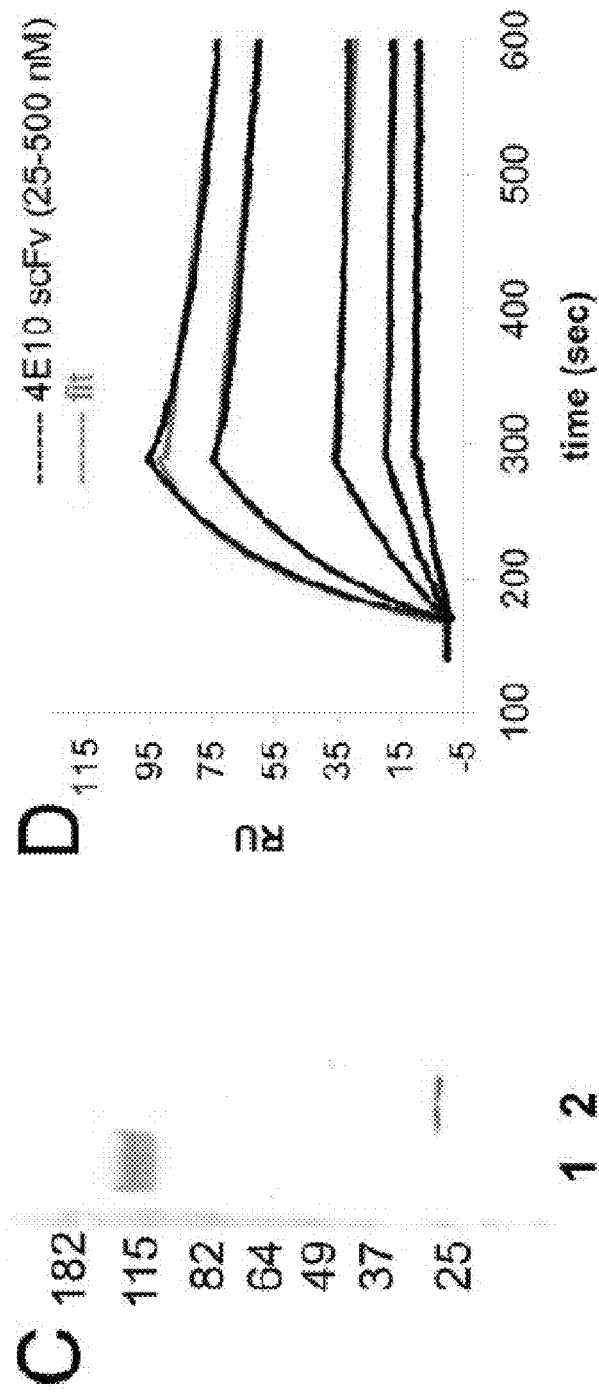

| Immobilized ligand | Flowing analyte | ka1 (1/Ms) | ka2 (1/s) | kd1 (1/s) | kd (1/s) | Kd (M) |
|---|---|---|---|---|---|---|
| 92UGgp140-Fd | 4D sCD4 | 2.39E5 | 2.11E-2 | 1.41E-2 | 7.38E-4 | 1.98E-9 |
| 92UGgp140-Fd | 2G12 Fab | 5.35E4 | | 9.58E-4 | | 1.79E-8 |
| b12 IgG | 92UG gp120 | 1.50E4 | | 1.49E-2 | | 9.93E-7[a] |
| b6 IgG | 92UG gp120 | 5.62E4 | | 1.51E-4 | | 2.69E-9[a] |
| 15e IgG | 92UG gp120 | 4.85E4 | | 3.18E-3 | | 6.57E-8[a] |
| 2F5 Fab | 92UGgp41-inter-Fd | 1.00E4 | | 1.39E-5[b] | | 1.38E-9 |
| 2F5 Fab | HXB2gp41-inter-GCN4 | 6.82E3 | | 6.11E-5[b] | | 8.96E-9 |
| 92UGgp41-inter-Fd | 2F5 Fab | 1.53E5 | | 4.96E-4 | | 3.24E-9 |
| 2F5 Fab | T20 | 4.54E5 | | 2.17E-3 | | 4.79E-9 |
| 2F5 Fab | 2F5 epitope peptide[c] | 8.59E5 | | 3.29E-3 | | 3.83E-9 |
| 2F5 epitope peptide[c] | 2F5 Fab | 2.82E5 | | 1.50E-3 | | 5.33E-9 |
| 92UGgp41-inter-Fd | 4e10scFv | 1.60E5 | | 1.71E-4 | | 1.07E-9[a] |
| His-4e10scFv | HXB2gp41-interf-GCN4 | 1.49e5 | | 4.43e-4 | | 2.98e-9[a] |
| 4e10 epitope peptide[d] | 4e10scFv | 3.69E4 | | 6.85E-4 | | 1.86E-8 |
| 2F5 Fab | 92UGgp41-post | 1.66E3 | | 2.43E-3 | | 1.41E-6 | unfolded 92UG-gp140-Fd on a western blot (FIG. 3A, inset, lane 1; FIG. 4C). The native trimer did not, however, bind mAb 2F5 under any of the conditions that were tested by SPR. In particular, 92UG-gp140-Fd exhibited no interaction with a 2F5 surface, regardless of whether IgG or Fab was used for immobilization (FIG. 3A). Also, no binding of 2F5 IgG or Fab with immobilized gp140, at either 20° or 37° C., was observed. The presence or absence of the foldon tag had no effect, nor did partial plasmin cleavage (FIG. 3A). The 92-gp140-Fd trimer also failed to bind 4E10 Fab and showed only very weak binding if any at all to 4E10 IgG at high concentration (FIG. 4A and FIG. S2H). Without intending to be bound by scientific theory, it was concluded that the epitopes of 2F5 and 4E10 were either buried or in a non-antigenic configuration on the native gp140 trimer. This conclusion is consistent with published reports that mAb 2F5 does not bind the envelope protein on the surface of virions (Cavacini et al. (2002) *AIDS* 16:2409; Hart et al. (2003) *J. Gen. Virol.* 84:353). Other published experiments suggest a temperature-sensitive interaction with cell-surface expressed Env, but the structural heterogeneity of cleaved envelope protein on cell surfaces and the potential lipid-binding ability of 2F5 make those results difficult to interpret (Finnegan et al. (2002) *J. Virol.* 76:12123; Sattentau et al. (1995) *Virology* 206:713; Haynes et al. (2005) *Science* 308:1906). Those gp140 preparations reported to bind 2F5 all contain significant amounts of monomers, dimers, or aggregates (Schulke et al. (2002) *J. Virol.* 76:7760; Jeffs et al. (2004) *Vaccine* 22:1032; Dey et al. (2007) *Virology* 360:199).

If mAbs 2F5 and 4E10 do not bind the ectodomain of the (gp120/gp41)$_3$ in the prefusion conformation found on virions, how do they neutralize? Previous attempts to mimic the intermediate state have been limited largely to constructs containing only the HR1 and HR2 fragments (Eckert et al. (1999) *Cell* 99:103; Root et al. (2001) *Science* 291:884; Binley et al. (2003) *J. Virol.* 77:5678; de Rosny et al. (2004) *J. Virol.* 78:2627), which could not be used to resolve the issue. In contrast, the gp41-inter constructs described herein contained nearly the full-length gp41 ectodomain, including the full epitopes for 2F5 and 4E10. The data in FIGS. 3B and 7B show that the Fab fragment derived from mAb 2F5 bound gp41-inter proteins very tightly ($K_d$<10 nM, with an off rate slower than $1.4 \times 10^{-5}$ s$^{-1}$), regardless of the choice of isolate and trimerization tag (Table 1) (The Fab was used to avoid potential avidity effects with intact antibody). The estimated dissociation constant was relatively insensitive to which protein was immobilized on the chip. The complex of 2F5 Fab and 92UGgp41-inter protein could also be purified by gel-filtration chromatography. The 4E10 single-chain Fv fragment (scFv) likewise showed very strong binding to gp41-inter proteins ($K_d$~1.1-2.9 nM; FIGS. 4B and 7D; Table 1). ScFv was used because 4E10 Fab produced by papain-digestion showed weaker neutralizing activity than those of scFv and IgG, while the latter two were equally potent. These observations indicate that 2F5 and 4E10 exerted their neutralizing activity by binding an intermediate conformation of gp41. Kinetic studies of membrane fusion have shown that both 2F5 and 4E10, like T20, are probably effective only during a small time interval during the fusion process (Binley et al. (2003) *J. Virol.* 77:5678; Dimitrov et al. (2007) *Biochemistry* 46:1398). Moreover, mutations in the gp41 core that destabilize the six-helix bundle conformation enhance sensitivity of the mutant viruses to 2F5 neutralization (Follis et al. (2002) *J. Virol.* 76:7356).

Peptides that contained the 2F5 epitope, such as T-20, bound the 2F5 Fab, as expected (FIG. 3D and Table 1), but they dissociated much more rapidly than did the gp41-inter proteins (Table 1). A rapid off rate has also been reported when the 2F5 epitope peptide is inserted into protein scaffolds other than gp41-inter (Ho et al. (2005) *Vaccine* 23:1559). Likewise, a peptide containing the full 4E10 epitope also showed weaker binding to 4E10 scFv ($K_d$~18 nM) than did gp41-inter (FIG. 4D and Table 1). Thus, without intending to be bound by scientific theory, very strong binding by these two mAbs appears to be a specific consequence of incorporating the epitope into a prehairpin intermediate conformation.

As expected, the postfusion state of gp41 bound the 2F5 Fab very weakly ($K_d$~1.4 μM; Table 1; FIG. 7C), while a short epitope peptide ending with the same residue as gp41-post showed much tighter binding ($K_d$~3.8-5.3 nM; Table 1; FIG. 8D), indicating that the 2F5 epitope in gp41-post did not have an optimal binding conformation. This result is consistent with observations that the formation of the six-helix bundle weakens 2F5 binding (Gorny and Zolla-Pazner (2000) *J. Virol.* 74:6186).

Example 3

Discussion

The results presented herein indicate that 2F5 and 4E10 inhibit HIV-1 infection by binding to their epitopes as displayed on the prehairpin intermediate conformation of gp41, thereby blocking a crucial step in the conformational transition required for membrane fusion. Binding may not obstruct formation of the six-helix bundle, however, as the epitopes lie outside HR2. That is, the block may occur at a very late step in the "zipping up" of gp41. Without intending to be bound by scientific theory, these two antibodies could, for example, prevent MPER from interacting with residues proximal to the fusion peptide, a potentially required step for induction of membrane hemifusion. The non-neutralizing, cluster I antibodies bound gp41-inter as well as prefusion gp 140 (FIGS. 6G and 7C). Thus, binding to the intermediate conformation is not by itself sufficient for neutralization. Because their target is a transient intermediate, 2F5 and 4E10 have a relatively narrow "window of opportunity." Both antibodies, which recognize linear epitopes adjacent to each other in the MPER of gp41, have long, hydrophobic heavy-chain CDR3 loops. These loops contact bound MPER peptides only at their base, and it has been proposed that they also interact with the viral membrane (Ofek et al. (2004) *J. Virol.* 78:10724; Cardoso et al. (2005) *Immunity* 22:163). Without intending to be bound by scientific theory, the putative, relatively non-specific membrane binding may simply concentrate the antibody to give it a kinetic head start during the short lifetime of the intermediate. Indeed, both 2F5 and 4E10 Fab fragments bind gp41-inter with high affinity in the absence of a lipid bilayer, consistent with a largely kinetic role for any membrane interaction.

Haynes and colleagues have found that 2F5 and 4E10 have properties resembling those of autoreactive antibodies (including their long, heavy-chain CDR3 loops) and that they interact with phospholipids (Haynes et al. (2005) *Science* 308:1906). They suggest that these characteristics might lead to elimination of such heavy chains from the available repertoire, increasing the challenge of making immunogens to elicit MPER-reactive responses. The data presented herein provides an additional explanation for the rarity of 2F5-like antibodies in HIV infected individuals. The estimated exposure time for a T-20 target site during cell-cell fusion is about 15 minutes (Muñoz-Barroso et al. (1998) *J. Cell Biol.* 140, 315-323). Recent estimates for the lifetime of an intermediate sensitive to the construct known as "5-helix" (a single-chain model for five of the six helices in the postfusion bundle) are much lower, on the order of only 5-10 seconds (Steger and Root (2006) *J. Biol. Chem.* 281:25813). In either case, the transient conformation would not have a long enough lifetime to be effective in inducing a host response. Moreover, it would be present only at the interface of an infecting virion with a T-cell or macrophage, inaccessible to the B-cell receptor that must initiate clonal proliferation and antibody synthesis.

Various examples from other viruses illustrate that the relevant conformation of a viral envelope protein must be presented, if immunogen design is the goal. The exposure of flavivirus neutralizing epitopes depends on whether the E protein is in a pre- or post-fusion conformation (Modis et al. (2004) *Nature* 427:313). A similar conclusion follows from the mapping of antigenic sites on the surfaces of pre- and post-fusion vesicular stomatitis virus (VSV) glycoprotein G (Roche et al. (2007) *Science* 315:843) and from early studies on antigenicity of influenza virus (Daniels et al. (1983) *J. Gen. Virol.* 64 (Pt 8):1657). HIV-1 Env-based protein immunogens often induce high ELISA-titer antibody responses with limited neutralizing activity and breadth (Bower et al. (2006) *Vaccine* 24:5442), but lack of rigorously characterized preparations of the envelope proteins in well-defined conformational states has confused many analyses of antigenicity and immunogenicity. Preparations of recombinant gp140 are often mixtures of monomers and higher oligomers. Their conformation and physiological relevance are difficult to define. Even cell-associated or virion-associated envelope proteins are structurally heterogeneous because of the tendency for gp120 to dissociate and because of inefficient cleavage of the precursor. Accordingly, the preparations described herein are a useful standard against which to evaluate future immunogens. The tight binding of 2F5 to gp41-inter provides evidence for the significance of an extended, prehairpin intermediate in the fusion transition. Moreover, gp41-inter may provide a scaffold for presenting the MPER in a conformation relevant to neutralization and potentially for inducing a relevant B-cell response.

Example 4

Materials and Methods

Expression Constructs

Expression constructs were generated by standard PCR techniques. Constructs for fusion proteins were made either by overlapping PCR or by ligation of compatible restriction fragments. pET21-a(+) and pET23-a(+) (Novagen, La Jolla, Calif.) were used for expression of 92UG-gp41-inter, and of HXB2-gp41-inter, 92UG-gp41-post, respectively, in *E. coli*. PFastBac-1 (Invitrogen, Carlsbad, Calif.) was the expression vector for gp140, gp140-Fd constructs in insect cells. P92UG-gp140 contains residues 26-675 (92UG037.8 numbering), followed by four residues introduced by restriction sites EcoR I and XbaI, a factor Xa site and a His-tag (-EFS-RIEGRHHHHHH (SEQ ID NO:7)). P92UG-gp140-Fd includes residues 26-675, followed by four residues introduced by restriction sites EcoRI and XbaI, a factor Xa site, the foldon tag and a His-tag (EFSRIEGRGSGGYI-PEAPRDGQAYVRKDGEWVLLSTFLGHHHHHH (SEQ ID NO:8)). P92UG-gp41-inter-Fd begins with residues 612-657 (HR2) and a linker (GGSGG (SEQ ID NO:9)), followed by residues 531-675, the foldon tag and a His-tag (GTGGSG-GYIPEAPRDGQAYVRKDGEWVLLSTFLGHHHHHH (SEQ ID NO:10)). Due to the initial confusion about the Env clone used, the primers for PCR reactions were designed based on the sequence of another 92UG037 isolate (GenBank No. U51190). As a result, following changes were introduced in the p92UG-gp41-inter-Fd: residues 533 (V to A), 612 (R to D), 651 (E to D) and 689 (N to K). P92UG-gp41-post contains residues 526-573, a linker (SGGRGG (SEQ ID NO:11)) and residues 620-660. PHXB2-gp41-inter-GCN4 begins with residues 620-661 (HR2, HXB2 numbering), a linker (SG-GRGG (SEQ ID NO:12)), followed by residues 546-678, and finally the GCN4 trimerization domain (IEDKIEEIL-SKIYHIENEIARIKKLIGE (SEQ ID NO:13)). PHXB2-gp41-interf-GCN4 is essentially identical as pHXB2-gp41-inter-GCN4 except the C-terminal end of gp41 ectodomain was extend to residue 683 to include the full epitope for mAb 4E10. The constructs were verified by restriction digestion and DNA sequencing.

Expression in *E. coli* and Protein Refolding

Gp41-inter and gp41-post constructs were expressed in *E. coli* using Rosetta (DE3)pLysS cells, which supply tRNAs for rare codons. Bacterial cultures were induced at an OD600 of 1.0 by addition of 1 mM isopropyl-D-thio galactopyranoside (IPTG). Cells were harvested 2-3 hours post-induction by centrifugation. Cell pellets were frozen at −80° C. Env constructs were insoluble when expressed in *E. coli*. Cells were lysed by three cycles of freezing-thaw in PBS with 0.4 mg/ml DNase I, 0.4 mg/ml RNase A, 2 mg/ml lysozyme, followed by brief sonication. For his-tagged constructs, inclusion bodies were spun down by centrifugation, and solubilized in 6 M guanidine hydrochloride (GdnHCl). After removing insoluble materials, the supernatant was loaded onto a Ni-NTA resin, washed with 6M GdnHCl, eluted with 300 mM imidazole in 6 M GdnHCl. The fractions containing His-tagged protein were pooled and the protein refolding initiated by rapid dilution of the pooled fractions into ice-cold refolding buffer (1 M arginine, 100 mM Tris-HCl pH 7.5, 2 mM EDTA, 0.2 mM oxidized glutathione, 2 mM reduced glutathione, one protease cocktail tablet (Roche, Basel, Switzerland)) at a final protein concentration of 100 μg/ml. The refolding mix was stored at 4° C. for at least 24 hours. The refolding reaction was then dialyzed against PBS four times and purified by a Ni-NTA column under native conditions. The imidazole-eluted fractions were pooled, concentrated, and further separated away from aggregated species by gel-filtration chromatography on Superdex 200 (GE Healthcare, United Kingdom) with a buffer containing 25 mM Tris-HCl (pH 7.5) and 150 mM NaCl. The purified protein was concentrated and stored at −80° C. Non-his-tagged gp41 constructs was purified be an acid-extraction method described in Frey et al. ((2006) *Proc. Natl. Acad. Sci. USA* 103:13938). The protein refolding proceeded the same way described above, except that refolding mix after dialysis was concentrated by ultrafiltration using Centriconplus-70 (Millipore).

Expression in Insect Cells and Protein Purification

The gp140 proteins were expressed in insect cells using the Bac-to-Bac system (Invitrogen) as described (Chen et al. (2000) *J. Biol. Chem.* 275:34946). Briefly, recombinant baculovirus was generated according to the manufacturer's protocol and amplified in Sf9 insect cells. The optimal amount of virus and post-infection harvest time was determined by small-scale tests in 6-well plates. For large-scale production, 12 L of Sf9 or *T. ni* (Hi-5) cells (2×10$^6$ cells/ml) were infected at the optimal MOI. The supernatant was harvested 72 hours post-infection by centrifugation and concentrated to 2 L in a tangential flow filtration system, ProFlux M12 (Millipore), followed by immediately exchanging into PBS in the ProFlux M12. After a clarifying spin and adding imidazole to the final concentration of 15 mM, the supernatant was loaded onto a nickel column at a flow rate of 1 ml/min, then washed with 15 mM imidazole in PBS, followed by further washing with 40 mM imidazole in PBS. The protein was eluted with 300 mM imidazole in PBS. The fractions containing the purified protein were pooled, concentrated, and further purified by gel filtration chromatography on Superose 6 (GE Healthcare). The protein was concentrated, frozen in liquid nitrogen and stored at −80° C.

Production of Monoclonal Antibody and Fab Fragments

Monoclonal antibodies were purified from cell supernatants of hybridomas growing in roller bottles using a 5 ml GammaBind Plus Sepharose affinity column as described previously (Chen et al. (2000) *J. Biol. Chem.* 275:34946). The 2G12 Fab was kindly provided by Robyn Stanfield, Ian Wilson and Dennis Burton at Scripps. 2F5 Fab fragment was produced by digestion of IgG with Endoproteinase Lys-C (Roche) as published (Ofek et al. (2004) *J. Virol.* 78:10724). 4E10 Fab was generated using a protocol modified from Cardoso et al. ((2005) *Immunity* 22:163). Briefly, 4E10 IgG was digested by activated papain (Sigma) in 20 mM sodium phosphate, pH 7.0 and 10 mM EDTA. The digest was then dialyzed against 0.1 M sodium acetate, pH 5.5 overnight. The Fab was purified on a protein A column using buffers supplied in ImmunoPure Fab Preparation Kit (Pierce). The flow-through from the protein A column was concentrated and further purified by a Superdex 200 column using 200 mM sodium acetate, pH 5.5 as a running buffer. All the purified Fabs were analyzed by SDS-PAGE under both reducing and non-reducing conditions. Production and characterization of 4E10 single chain Fv fragment was performed. Briefly, 4E10 scFv with a C-terminal His-tag was cloned into pET-21a(+) vector and expressed in *E. coli*. The protein was refolded and purified following the same protocol for 92UGgp41-inter-Fd (see Expression in *E. coli* and protein refolding).

Chemical Crosslinking, Analytical Ultracentrifugation (AUC) and Circular Dichroism Spectroscopy Chemical crosslinking, analytical ultracentrifugation (AUC) and circular dichroism spectroscopy were carried out as described previously (Chen et al. (2000) *J. Biol. Chem.* 275:34946).

Surface Plasmon Resonance Binding Assays

All experiments were performed in duplicate with a Biacore 3000 instrument (Biacore Inc.) at 20° C. in HBS-EP running buffer (10 mM HEPES pH 7.4, 150 mM NaCl, 3 mM EDTA, 0.005% surfactant P20). Immobilization of ligands to CM5, NTA and SA chips (Biacore Inc.) followed the standard procedures recommended by manufacture. Immobilization of 4E10 antibody to a CM5 chip by the standard amine coupling procedure was found to block binding to its antigens and the same protocol to couple 92UGgp140-Fd trimer to a CM5 chip also has a denaturing effect on the trimer. These two types of immobilization were therefore not used in the subsequent experiments. The final immobilization levels were between 300 and 500 RU to avoid rebinding events. For kinetic measurements, sensorgrams were obtained by passing various concentrations of an analyte over the ligand surface at a flow rate of 50 μl/min using a 2 minute association phase and a 10 minute dissociation phase. The sensor surface was regenerated between each experiment using a single injection of 35 mM NaOH, 1.3 M NaCl; or 10 mM HCl, 1.3 M NaCl, at a flow rate of 100 μl/minute. Identical injections over blank surfaces were subtracted from the data for kinetic analysis. Binding kinetics was evaluated using BiaEvaluation software (Biacore Inc.).

Negative-Stain Electron Microscopy

92UGgp41-inter protein was negatively stained with uranyl formate as described (Ohi et al. (2004) *Biol. Proceed. Online* 6:23). Images were recorded by a Tecnai T20 microscope operated at 120 kV with a magnification of 50K, and by a Gatan 4K×4K CCD camera with a defocus of 1.5 μm following a low-dose procedure. All images were binned 2×2 to a final pixel size of 4.5 Å/pixel at specimen level. Individual particles were selected manually and processed with SPIDER (Frank et al. (1996) *J. Struct. Biol.* 116:190).

What is claimed:

1. An isolated, antigenic human immunodeficiency virus type 1 (HIV-1) gp41 fusion polypeptide capable of forming a prehairpin intermediate conformation comprising the following structure: $NH_2$-heptad repeat 2 (HR2)-linker-heptad repeat 1 (HR1)-C-C-immunodominant loop region-HR2-membrane proximal external region (MPER)-COOH, wherein said fusion peptide is capable of inducing a broadly anti-HIV-1 neutralizing antibody when injected into a subject.

2. The polypeptide of claim 1, further comprising an oligomerization domain carboxy terminal to the membrane-proximal external region.

3. The polypeptide of claim 2, wherein the oligomerization domain is a trimerization domain.

4. The polypeptide of claim 1, further comprising a protein tag carboxy terminal to the membrane-proximal external region.

5. The polypeptide of claim 1, wherein the polypeptide elicits production of a broadly neutralizing antibody when injected into a subject.

6. An immunogenic composition comprising an isolated antigenic human immunodeficiency virus type 1 (HIV-1) gp41 fusion polypeptide capable of forming a prehairpin intermediate conformation comprising the following structure: $NH_2$-heptad repeat 2 (HR2)-linker-heptad repeat 1 (HR1)-C-C-immunodominant loop region-HR2-membrane proximal external region (MPER)-COOH, and a pharmaceutically acceptable carrier.

* * * * *